US006632808B1

(12) United States Patent
Caughey et al.

(10) Patent No.: US 6,632,808 B1
(45) Date of Patent: Oct. 14, 2003

(54) INHIBITORS OF AMYLOID FORMATION

(75) Inventors: Winslow S. Caughey, Hamilton, MT (US); Byron Caughey, Hamilton, MT (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/762,725

(22) PCT Filed: Aug. 11, 1999

(86) PCT No.: PCT/US99/18297

§ 371 (c)(1),
(2), (4) Date: Mar. 7, 2001

(87) PCT Pub. No.: WO00/09111

PCT Pub. Date: Feb. 24, 2000

Related U.S. Application Data

(60) Provisional application No. 60/096,148, filed on Aug. 11, 1998.

(51) Int. Cl.[7] ..................... A61K 31/409; C07D 487/22
(52) U.S. Cl. ..................... 514/185; 514/410; 540/122; 540/145
(58) Field of Search ................ 514/185, 410; 540/122, 145

(56) References Cited

U.S. PATENT DOCUMENTS

| | | | |
|---|---|---|---|
| 4,961,920 A | 10/1990 | Ward | 424/9 |
| 5,066,274 A | 11/1991 | Bommer et al. | 604/20 |
| 5,081,115 A | 1/1992 | Vreman et al. | 514/185 |
| 5,095,030 A | 3/1992 | Levy et al. | 514/410 |

FOREIGN PATENT DOCUMENTS

| | | |
|---|---|---|
| FR | 2 676 738 | 5/1991 |
| WO | WO9107406 | 5/1991 |
| WO | WO9401116 | 1/1994 |
| WO | WO9510185 | 4/1995 |
| WO | WO9531197 | 11/1995 |
| WO | WO9640223 | 12/1996 |
| WO | WO9716728 | 5/1997 |
| WO | WO9835236 | 8/1998 |
| WO | WO9955388 | 11/1999 |

OTHER PUBLICATIONS

Caughey et al., "Heme A of Cytochrome c Oxidase," *The Journal of Biological Chemistry*, 250(19):7602–7622 (1975).

(List continued on next page.)

*Primary Examiner*—Richard L. Raymond
(74) *Attorney, Agent, or Firm*—Klarquist Sparkman, LLP

(57) ABSTRACT

Methods, compounds and compositions are disclosed for treating amyloidogenic diseases, like Alzheimer's disease and type 2 diabetes, and particularly prion diseases associated with conversion of protease sensitive PrP (PrP-sen) to protease resistant PrP (PrP-res), by administering therapeutically effective amounts of a tetrapyrrole. Particular disclosed tetrapyrroles having this activity include phthalocyanines, deuteroporphyrins, and meso-substituted porphines. Complexes of certain of the pyrroles with metals or metal ions produce compounds that are particularly effective in converting the conversion of PrP-sen to PrP-sen. The treatment of the present invention is particularly suited for preventing or inhibiting the progression of prion related diseases, such as transmissible spongiform encephalopathies.

70 Claims, 4 Drawing Sheets

OTHER PUBLICATIONS

Howlett et al., "Hemin and related porphyrins inhibit β–amyloid aggregation," *FEBS Letters*, 417:249–251 (1997).

Paris et al., "Role of Peroxynitrite in the Vasoactive and Cytotoxic Effets of Alzheimer's β–Amyloid$_{1-40}$ Peptide," *Experimental Neurology*, 152:116–122 (1998).

Melov et al., "A novel neurological phenotype in mice lacking mitochondrial manganese superoxide dismutase," *Natural Genetics*, 18:159–163 (1998).

Caughey et al., "Inhibition of protease–resistant prion protein formation by porphyrins and phthalocyanines," *Proc. Natl. Acad. Sci. USA*, 95:12117–12122 (1998).

Priola et al., "Novel therapeutic uses for porphyrins and phthalocyanines in the transmissible spongiform encephalopathies," *Microbiology*, 2:563–566 (1999).

Gilbert et al., "Inhibitors of protease–resistant prion formation," *International Antiviral News*, 7(5):78–82 (1999).

Henke, "Superoxide dismutase mimics as future therapeutics," *Exp. Opin. Ther. Patents*, Ashley Publications Ltd., 9(2):169–180 (1999).

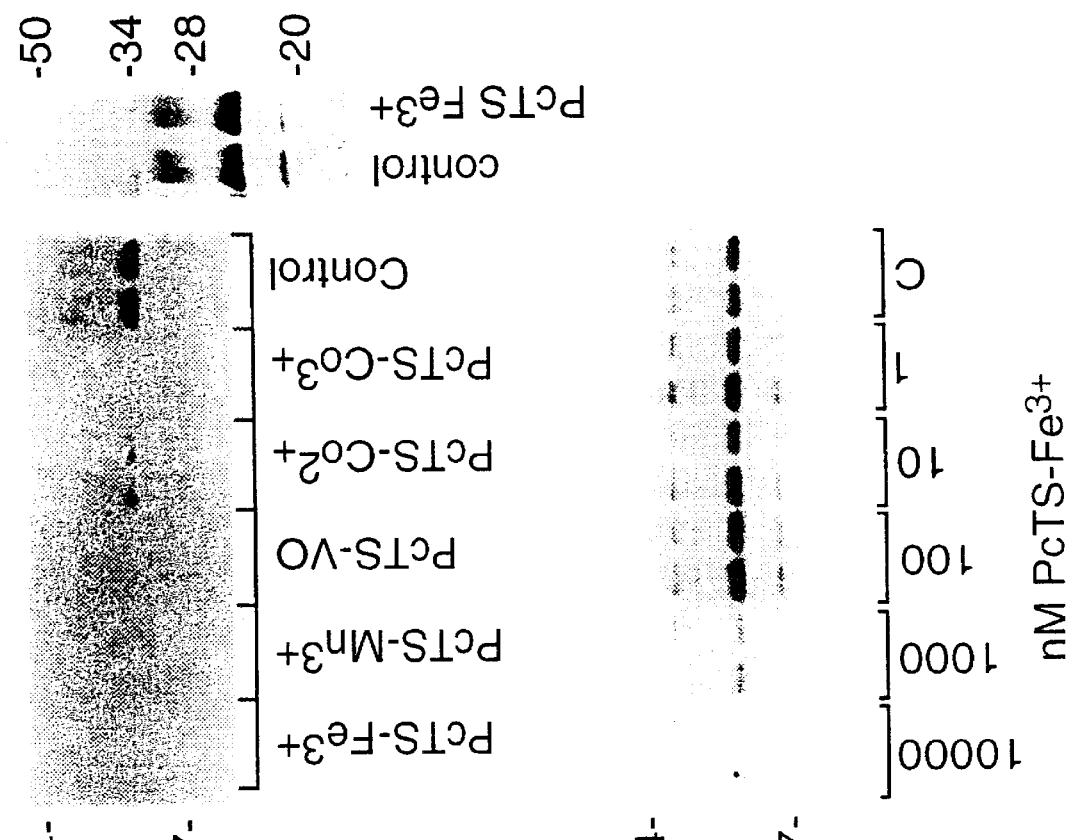

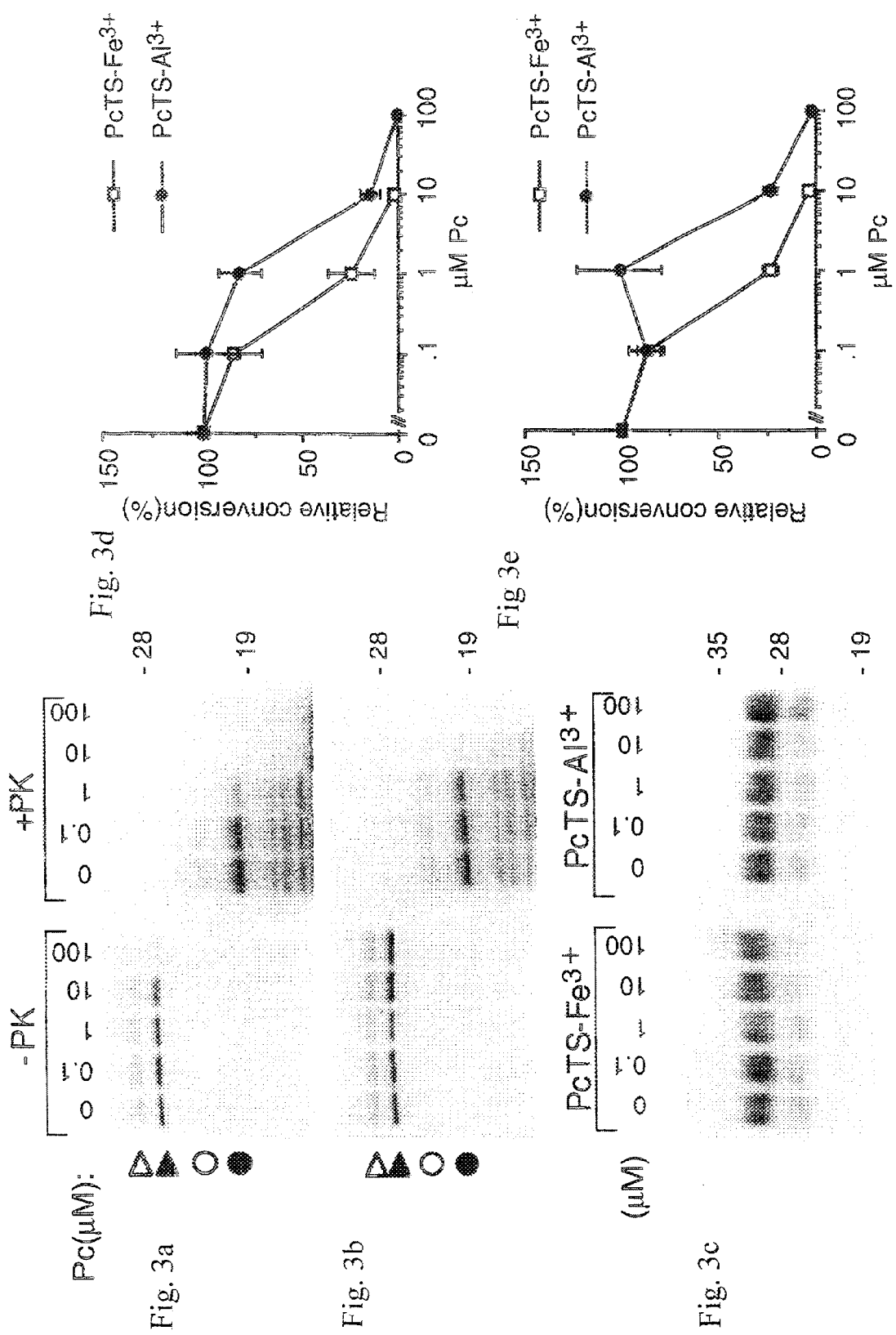

INHIBITORS OF AMYLOID FORMATION

PRIORITY CLAIM

This application is a U.S. national stage application of PCT/US99/18297, filed Aug. 11, 1999, which was published in English under PCT Article 21(2), which in turn claims the benefit of U.S. Provisional Application No. 60/096,148, filed Aug. 11, 1998.

FIELD OF THE INVENTION

This invention concerns pharmaceutical compositions that are useful for inhibiting formation of amyloid deposits in amyloidogenic disorders, such as those deposits associated with protease resistant prion proteins in transmissible spongiform encephalopathies.

BACKGROUND OF THE INVENTION

Amyloid formation is found in a number of disorders, such as diabetes, Alzheimer's Disease (AD), scrapie, Gerstmann-Staussler-Scheinker (GSS) Syndrome, bovine spongiform encephalopathy (BSE), Creutzfeldt-Jakob disease (CJD), chronic wasting disease (CWD), and related transmissible spongiform encephalopathies (TSEs). These and other diseases in which amyloid plaques or amyloid deposits are formed in the body are referred to as amyloidogenic diseases.

Transmissible spongiform encephalopathies are fatal neurodegenerative diseases that include such human disorders as CJD, kuru, fatal familial insomnia, and GSS. Animal forms of TSE include scrapie in sheep, CWD in deer and elk, and bovine spongiform encephalopathy in cattle. These diseases are characterized by the formation and accumulation in the brain of an abnormal proteinase K resistant isoform (PrP-res) of a normal protease-sensitive host-encoded prion protein (PrP-sen). PrP-res is formed from PrP-sen by a post-translational process involving conformational changes that convert the PrP-sen into a PrP-res molecular aggregate having a higher β-sheet content. The formation of these macromolecular aggregates of PrP-res is closely associated with TSE-mediated brain pathology in which amyloid deposits of PrP-res are formed in the brain, which eventually becomes "spongiform" (filled with holes).

In the past, the TSE diseases were a medical curiosity because the transmissible agent was difficult to inactivate with heat, radiation or chemicals that would be expected to inactivate infectious living organisms such as bacteria and viruses. Instead, this class of diseases appeared to be transmitted by exposure to an unusual agent, for example by ritual cannibalism in the Foret people of New Guinea, or feeding of animal parts to cattle in bovine spongiform encephalopathy (BSE), Iatrogenic CJD has also been caused by administration of human growth hormone derived from cadaveric pituitaries, transplanted dura mater and corneal grafts, as well as exposure of surgeons to affected tissue during neurological procedures. The TSE diseases took on new urgency, however, when it appeared that cross-species infection of humans in Europe may have occurred, perhaps from the ingestion of beef from affected cows. That development has further stimulated an international search for a better understanding of the pathophysiological mechanism of the disease, and possible treatments.

The presence of a native prion protein (PrP) has been shown to be essential to pathogenesis of TSE. The cellular protein PrP-sen is a sialoglycoprotein encoded by a gene that in humans is located on chromosome 20. The PrP gene is expressed in neural and non-neural tissues, with the highest concentration of its mRNA being in neurons. The translation product of the PrP gene consists of 253 amino acids in humans, 254 in hamsters and mice, 264 amino acids in cows, and 256 amino acids in sheep (all of these sequences are disclosed in U.S. Pat. No. 5,565,186, which describes methods of making transgenic mice that express species specific PrP). In prion protein related encephalopathies, the cellular PrP-sen is converted into the altered PrP-res that is distinguishable from PrP-sen in that PrP-res aggregates (Caughey and Chesebro, 1997, *Trends Cell Biol.* 7, 56–62); is proteinase K resistant in that only approximately the N-terminal 67 amino acids are removed by proteinase K digestion under conditions in which PrP-sen is completely degraded (Prusiner et al., 1996, Sem. Virol. 7, 159–173); and has an alteration in protein conformation in which the amount of α-helical conformation for PrP-sen is reduced, and the amount of β-sheet conformation for PrP-res is increased (Pan et al., 1993, *Proc. Natl. Acad. Sci. USA* 90, 10962–10966).

If PrP-sen is not expressed in the brain tissue of animal recipients of scrapie-infected neurografts, no pathology occurs outside the graft, demonstrating that PrP-res and PrP-sen are both required for the pathology (Brander et al., *Nature* 379:339–343, 1996). The long latency period between infection and the appearance of disease (months to decades depending on species) has prompted the development of a cell-free in vitro test, in which PrP-res induces the conversion of PrP-sen to PrP-res (Kocisko et al., *Nature* 370:471474, 1994). See also Prusiner et al., WO 97/16728 published May 9, 1997. The in vitro interaction between PrP-res and PrP-sen occurs with species and strain specificities that mimic TSE species barrier effects and strain differences in vivo (Kocisko et al., 1995, *Proc Natl Acad Sci USA* 92, 3923–3927; Bessen et al., 1995, *Nature* 375, 698–700; Bossers et al., 1997, *Proc. Natl. Acad. Sci. USA* 94, 49314936; Raymond et al., 1997, *Nature* 388, 285–288), hence in vitro cell free culture techniques are considered to accurately predict pathological developments in the brains of infected animals. These in vivo and in vitro observations indicate that direct interactions between PrP-res and PrP-sen form PrP-res and promote TSE pathogenesis.

Small synthetic peptides containing certain PrP sequences have previously been shown to spontaneously aggregate to form fibrils with a high degree of β-sheet secondary structure of the type seen in the insoluble deposits in TSE afflicted brains (Gasset et al., 1992, *Proc. Natl. Acad. Sci. USA* 89, 10940–10944; Come et al., 1993, *Proc. Natl. Acad. Sci. USA* 90, 5959–5963; Forloni et al., 1993, *Nature* 362, 543–546; Hope et al., 1996, *Neurodegeneration* 5, 1–11). Moreover, other synthetic PrP peptides have been shown to interact with PrP-sen molecules to form an aggregated complex with increased protease-resistance (Kaneko et al., *Proc. Natl. Acad. Sci. USA* 92, 11160–11164, 1995; Kaneko et al., *J. Mol. Biol.* 270, 574–586, 1997).

The bovine spongiform encephalopathy epidemic and the appearance of the new variant of CJD in humans has heightened the urgency to develop therapies for the transmissible spongiform encephalopathies (TSE) or prion diseases. U.S. Pat. No. 5,134,121 disclosed the use of a nerve growth blocking peptide to treat prion associated diseases by inhibiting PrP-res formation in the infected host. Sulfated glycans and the sulfonated amyloid stain Congo Red are known inhibitors of PrP-res formation and scrapie agent replication in scrapie-infected neuroblastoma (ScNB) cells (Caughey and Chesebro, 1997, *Trends Cell Biol.* 7, 56–62; Caughey et al., 1992, *J. Neurochem.* 59, 768–771; Caughey et al., 1993, *J. Virol.* 67, 643–650; Caughey et al., 1993, *J. Virol.* 67, 6270–6272). These polyanions are also protective against scrapie in rodents if administered near the time of infection, but have less therapeutic benefit after the infection has reached the central nervous system (Ehlers and Diringer, 1984, *J. Gen. Virol.* 65, 1325–1330; Farquhar and Dickinson, 1986, *J. Gen. Virol.* 67, 463–473; Kimberlin and Walker, 1986, *Antimicrob. Agents Chemother.* 30, 409–413; Ingrosso et al., 1995, *J. Virol.* 69, 506–508). This problem, and/or inherent toxicity, also limit the utility of other classes of potential drugs, such as the polyene antibiotics (Demaimay et al., 1997 *J. Virol.* 71, 9685–9689) and anthracycline (Tagliavini et al., 1998, *Science* 276, 1119–1122).

Protohemin has been reported to inhibit a protein kinase that phosphorylates filament proteins in patients with Alzheimer' disease. (Vincent and Davies, 1992, *PNAS USA* 89:2878–82). Porphyrins and other tetrapyrroles have previously been used therapeutically against cancers and against viral infections (Schuitmaker et al., 1996, *J. Photobiol.* 34 (1): 3–12; Petho, 1995, *Acta Physiol. Hung.* 83(2): 113–119). A major therapeutic use has exploited the light absorbing qualities of these molecules to perform "photodynamic therapy" (PDT). In PDT, tissue is photosensitized with the porphyrin or other tetrapyrrole, by exposure to light of a particular wavelength. Absorption of light radiation causes destruction of the sensitized cells (Rebeiz et al., 1996, *Cancer Res.* 56(2): 399–344; Gomer et al., 1996, *J. Clin. Laser Med. Surg.* 14(5): 315–321; Fritsch et al., 1998, *Arch Dermatol* 134(2): 207–214). Alternatively, compounds such as aminolevulinic acid (ALA) may be used to promote the endogenous production of protoporphyrins, followed by photic stimulation and cell death (Schuitmaker et al., 1996, *J. Photobiol.* 34 (1): 3–12).

There is a need for agents that will specifically inhibit the formation of PrP-res from PrP-sen, and therefore prevent or slow the deposition of amyloid deposits in the tissues of animals that have been exposed to a TSE etiological agent, or are suffering from a neurodegenerative disorder having the characteristics of a spongiform encephalopathy. There also is a need for an agent that has a high inhibitory activity against PrP-res formation, that crosses the blood-brain barrier, and that has only minimum cytotoxic effect, without a detrimental effect on the rate of natural PrP-sen biosynthesis.

SUMMARY OF THE INVENTION

The present invention includes compositions and methods for preventing, or inhibiting, the progression of amyloidogenic diseases such as prion associated diseases in which PrP-sen is converted to PrP-res. The compositions of the invention include a pharmaceutically acceptable carrier and a therapeutically effective amount of a tetrapyrrole that inhibits progression of the amyloidogenic disease. In particular embodiments, the tetrapyrrole inhibits the conversion of protease sensitive prion protein (PrP-sen) to protease resistant prion protein (PrP-res).

Particularly disclosed tetrapyrroles include porphines, porphyrins, phthalocyanines, their anionic derivatives (such as sulfonated, carboxylated, and phosphorylated derivatives), their cationic derivatives (such as quaternized or protonated amines), and dervatives bearing uncharged polar groups such as hydroxyl. Particular examples of these tetrapyrroles include phthalocyanine sulfonates, deuteroporphyrins, and meso-substituted porphines. Some particularly disclosed embodiments are relatively stable and non-toxic (having low dark toxicity), and do not include protohemin or protohematin. The intrinsic lipophilicity of the tetrapyrroles makes them more likely to be delivered through the blood brain barrier than many other drugs, which is important in a disease such as TSE in which the most devastating effect of the disease is in the central nervous system. However, the therapeutic tetrapyrroles of the present invention can be delivered peripherally (for example via systemic administration to the lymphoreticular system, including the tonsils and spleen) without toxicity at reasonably high doses.

The invention also includes methods for treating or preventing progression of an amyloidogenic disease in an animal, by administering a therapeutically effective amount of a tetrapyrrole to the animal. In particular embodiments, the amyloidogenic disease is a disease in which inhibiting conversion of PrP-sen to PrP-res in an animal inhibits or prevents progression of the disease, such as a transmissible spongiform encephalopathy (TSE). In other embodiments, the disease is one involving pathological formation of amyloid depostis or plaques, such as Alzheimer□s disease or Type 2 diabetes.

In embodiments of the invention in which the tetrapyrrole is a phthalocyanine, the phthalocyanine may be a phthalocyanine sulfonate, such as a phthalocyanine monosulfonate, disulfonate, trisulfonate, or tetrasulfonate, and/or a metallophthalocyanine with a metal compound, such as VO, or a metal ion, such as a cation of iron, manganese, cobalt, nickel, zinc, and aluminum, occupying the center of the macrocyclic ring. In particular examples the metal compound or metal ion may be $Fe^{3+}$, $Mn^{3+}$, $Co^{3+}$, $Cu^{2+}$, $Ni^{2+}$, $Zn^{2+}$, $Co^{2+}$, $Al^{3+}$, or VO, and especially the subgroup $Fe^{3+}$, $Mn^{3+}$, $Co^{3+}$, $Cu^{2+}$, $Ni^{2+}$, and $Zn^{2+}$. In embodiments in which the tetrapyrrole is a tetrasulfonylphthalocyanine (PcTS), the particular PcTS includes metal-free PcTS, PcTS-$Fe^{3+}$, PcTS-$Mn^{3+}$, PcTS-$Co^{3+}$, PcTS-$Cu^{2+}$, PcTS-$Ni^{2+}$ and PcTS-VO.

In embodiments in which the tetrapyrrole is a deuteroporphyrin, the deuteroporphyrin may be a derivative substituted with, for example, a sulfato, a carboxylate, an acetyl, an oxime, a ketone, halogen or nitrate group, or derivatives thereof, or a hydroxyalkyl or polyhydroxyalkyl group, having for example, up to five carbons, and particularly three or fewer carbons (such as hydroxymethyl, hydroxyethyl, hydroxy propyl, dihydroxyethyl, and dihydroxypropyl). In particular embodiments, the derivative may be a sulfonate. For embodiments in which the deuteroporphyrin is complexed with a metal, the metal ion may be an iron ion, for example $Fe^{3+}$.

In those embodiments in which the tetrapyrrole is a meso-substituted porphine, the meso-porphine may, for example, be substituted at one or more of the meso positions with alkyl, phenyl, carboxyl, 2-pyridyl, 3-pyridyl, or 4-pyridyl groups, or combinations thereof. Phenyl groups at the meso positions may further be substituted with a carboxylate group, a sulfate group, secondary, tertiary, and quaternary amine groups, hydroxyl groups, or phosphate groups. Pyridyl groups at the meso positions may further be N-substituted with alkyl groups to form quaternary pyridinium ions. Alternatively, the basic pyridyl groups can be protonated at appropriate pH's to form cationic pyridinium groups. The meso-porphine may be a metalloporphine that is complexed with a metal compound (such as VO) or a metal ion selected from the group of iron, manganese, copper, nickel and zinc, ions and particularly a cation selected from the group of: $Fe^{3+}$, $Mn^{3+}$, $Co^{3+}$, $Cu^{2+}$, $Ni^{2+}$, $Zn^{2+}$, $Co^{2+}$ and $Al^{3+}$.

When administered as a therapeutic treatment, the tetrapyrrole may be administered at a dose between 1 nanogram and 0.5 to 1 gram per kg body weight (for example 1 microgram to 100 micrograms per kg) of the animal, without appreciable toxicity, such as cytotoxicity. Although the tetrapyrrole may be administered by a wide variety of routes (direct administration into the CNS, intracranial ventricular, intrathecal, aural, transdermal, intravenous, intramuscular, subcutaneous, oral, olfactory, ocular and rectal), the tetrapyrroles of the present invention are particularly advantageous because many of them are believed to readily pass the blood brain barrier. Compounds having increased lipophilicity, or in pharmaceutical carriers such as liposomes, will have enhanced penetration of the CNS.

The invention also includes methods of screening compounds which inhibit conversion of PrP-sen to PrP-res, by contacting PrP-sen with a tetrapyrrole or an analog or derivative or mimetic thereof, in a mixture of PrP-res and PrP-sen under conditions in which a conversion of PrP-sen to PrP-res would be expected to occur. The mixture is exposed to a sufficient concentration of proteinase K to proteolytically degrade PrP-sen after exposure of the proteinase K, and then an assay is performed to determine whether the conversion of PrP-sen to PrP-res has been inhibited. One such method for detecting this inhibition is by detecting the relative or complete disappearance of an electrophoretic band that corresponds to PrP-res, as an indication that the peptide inhibits conversion of PrP-sen to PrP-res.

BRIEF DESCRIPTION OF THE DRAWINGS

FIG. 1A shows a digital image of an immunoblot (with the primary antibody R30 against PrP-res) demonstrating inhibition of PrP-res accumulation (the band at about 27 kD) in ScNB cultures by sulfonated phthalocyanine (PcTS) compounds. Inhibitory effects are shown of PcTS compounds at 10 μM in the culture medium over 4 days.

FIG. 1B is a digital image of an immunoblot showing concentration dependent inhibitory effects of PcTS-$Fe^{3+}$, from concentrations of 0 to 10,000 nM.

FIG. 1C is a representation similar to FIG. 1B, showing inhibitory effects of treatment of ScNB cell lysates with 10 μM PcTS-$Fe^{3+}$ for 1-hour prior to PK treatment, and extraction for the detection of PrP-res by immunoblot.

FIGS. 3A–B are digital images of immunoblots showing inhibition of cell-free conversion of PrP-sen to PrP-res by PcTS-$Fe^{3+}$ (FIG. 3A) and by PcTS-$Al^{3+}$(FIG. 3B) under GdnHcl free conditions.

FIG. 3C is a digital image of an immunoblot analysis of PK-digested total PrP-res using monoclonal antibody 3F4 (which has an epitope within the normally PK resistant portion of PrP-res) in the presence of different concentrations of PcTS-$Fe^{3+}$ and PcTS-$Al^{3+}$.

FIGS. 3D and 3E are graphs showing the results of autoradiographic determination of inhibition of cell-free conversion of PrP-sen to PrP-res by PcTS-$Fe^{3+}$ and PcTrS-$Al^{3+}$ under GdnHCl-free (3D) or GdnHCl-containing conditions (3E). $^{35}S$-PrP-sen was incubated with unlabeled PrP-res for 2 days in the presence of the designated concentration of phthalocyanine.

DETAILED DESCRIPTION OF SEVERAL EMBODIMENTS

Abbreviations and Definitions

Figure 2A:
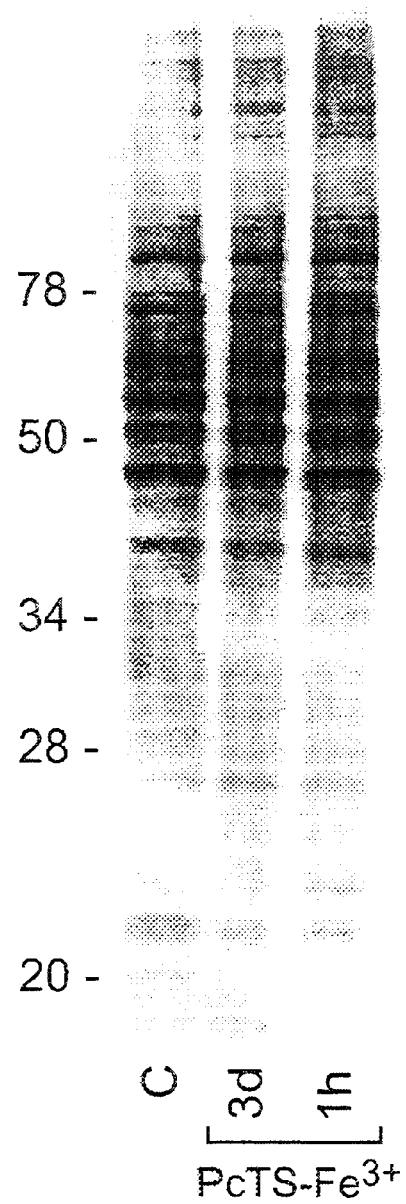
FIG. 2A is a digital image of phospho-autoradiographic images of $^{35}S$ metabolic labeling of total proteins in ScNB cells after pre-treatments with 10 μM PcTS-$Fe^{3+}$, showing that the presence of PcTS-$Fe^{3+}$ did not affect protein synthesis in the cell.
Figure 2B:
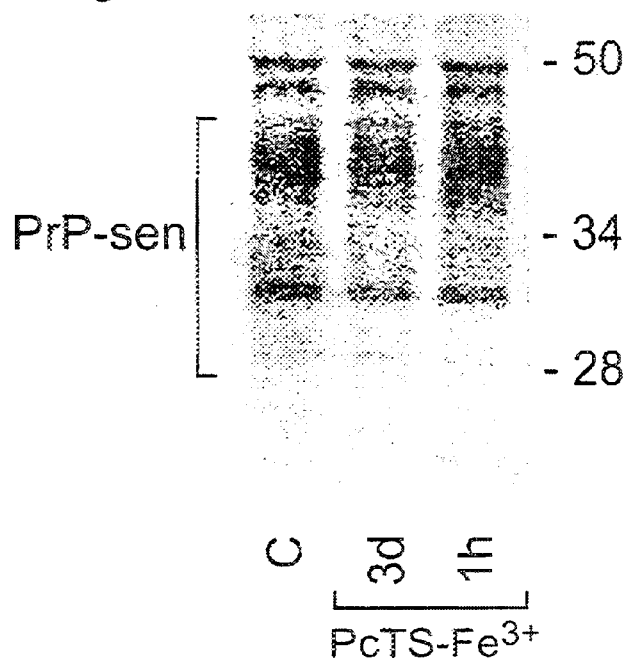
FIG. 2B shows digital images of phospho-autoradiographic images of $^{35}S$ metabolic labeling of PrP-sen proteins in ScNB cells after pretreatments with 10 μM PcTS-$Fe^{3+}$, indicating that addition of the PcTS-$Fe^{3+}$ did not affect PrP-sen protein synthesis.

The following abbreviations and definitions are used herein:

| | |
|---|---|
| AD | Alzheimer Disease |
| BSE | Bovine spongiform encephalopathy |
| CJD | Creutzfeldt-Jakob disease |
| DP | Deuteroporphyrin |
| Dpi | Days post infection |
| GSS | Gerstmann-Staussler-Scheinker |
| PrP | Prion protein |
| PrP-sens | PrP sensitive to Proteinase K degradation |
| PrP-res | PrP resistant to Proteinase K degradation |
| PK | Proteinase K |
| TSE | Transmissible spongiform encephalopathy |
| Pc | Phthalocyanine |
| PcTS | Phthalocyanine tetrasulfonate |
| PcTrS | Phthalocyanine trisulfonate |
| TPhP | Tetraphenyl porphyrin |
| TPyP | Tetrapyridyl porphyrin |
| ScNB | Scrapie-infected neuroblastoma |
| VO | Vanadyl (VO) |

Prion: An infectious agent believed to cause spongiform encephalopathies in animals (including humans). The term "prion" is a contraction of the words "protein" and "infection."

PrP protein: An animal protein that is the translation product of the PrP gene, wherein the protein consists of approximately 253 amino acids in humans (Kretzschamar et al., 1986, *DNA* 5: 315–324; Pucket et al., 1991, *Am. J. Hum. Genet.* 49: 320–329), 254 amino acids in hamster and mice, 264 amino acids in cows, and 256 amino acids in sheep (U.S. Pat. No. 5,565,186). The PrP protein includes a native PrP-sen isoform which is degraded by proteinase K, and a pathological PrP-res form which is not degraded by proteinase K, and which induces a conformational change in PrP-sen to form characteristic amyloid deposits of the type seen in the spongiform encephalopathies.

The term "PrP" refers generically to peptides from animal PrP, and includes specific human, hamster, murine, sheep, bovine or avian forms of the PrP. The region from positions 119–136 of the PrP is identical in humans (P113–136), mouse (P112–119), mink, rat, sheep (P115–122), cow (P123–130), Chinese hamster and Armenian hamster. Sequences are substantially homologous across even longer regions in different species.

Conditions that would be expected to convert PrP-sen to PrP-res: Such conditions are described in references (Raymond et al., *Nature* 388, 285–288, 1997; Kocisko et al., 1994, *Nature* 370, 471–474; Kocisko et al., 1995, *Proc. Natl. Acad. Sci. USA* 92, 3923–3927; Bessen et al., 1995 *Nature* 375, 698–700; Bossers et al., 1997, *Proc. Natl. Acad. Sci. USA* 94, 4931–4936) that teach a cell-free conversion assay in which PrP-sen is converted to PrP-res. The inhibition of the conversion reaction that would be expected to convert PrP-sen to PrP-res can be quantified, for example by determining the ratio between conversion in the presence of an inhibitory substance and the control conversion reaction in the absence of the inhibitory substance. Inhibition of "conversion" may be determined by the ratio between the PK-resistant 35S-labeled bands that are approximately 5–10 kDa lower in molecular mass than the non-digested 35S-PrP-sen as quantified by phosphor autoradiographic imaging analysis.

Amyloidogenic diseases: A heterogeneous group of hereditary and nonhereditary disorders related by their production of amyloid forming proteins. These disorders are often accompanied by extracellular deposition of amyloid plaques in one or more tissues. An amyloid plaque is identified by its amorphous, eosinophilic, homogenous appearance. A unique green birefringence after Congo Red staining, fibrillar ultrastructure, and cross beta X-ray diffraction pattern are also features of amyloid plaques. It is possible to clinically classify various amyloid proteins based on the nature of their biochemistry. Table 1 lists a variety of amyloidogenic diseases along with their associated amyloidogenic proteins:

TABLE 1

The 1990 guidelines for nomenclature and classification of amyloid and amyloidosis

| Amyloid Protein* | Protein Precursor | Clinical |
|---|---|---|
| AA** | ApoSAA | Reactive (secondary)<br>Familial Mediterranean Fever<br>Familial amyloid neuropathy with urticaria and deafness<br>(Muckle-Wells syndrome) |
| AL | kappa, lambda (e.g., k III) | Idiopathic (primary), myeloma or Macroglobulinernia-associated |
| AH | IgG 1 (γ1) | |
| ATTR | Transthyretin | Familial amyloid polyneuropathy (Portuguese)<br>Familial amyloid cardiomyopathy (Danish)<br>Systemic senile amyloidosis |
| AapoAI | ApoAI | Familial amyloid polyneuropathy (Iowa) |
| Agel | Gelsolin | Familial amyloidosis (Finnish) |
| Acys | Cystatin C | Hereditary cerebral hemorrhage with amyloidosis (Icelandic) |
| AB | B protein precursor (e.g., BPP 695) | Alzheimer's disease<br>Down's syndrome<br>Hereditary cerebral hemorrhage amyloidosis (Dutch) |
| $AB_2M$ | B2-microglobullin | Associated with chronic dialysis |
| Ascr | Scrapie protein, precursor 33-35f cellular form | Creutzfeldt-Jakob disease, etc.<br>Gerstmann-Staussler-Scheinker Syndrome |
| Acal | (Pro)calcitronin | Medullary carcinoma of thyroid |
| AANF | Atrial natriuretic factor | Isolated atrial amyloid |
| ALAPP | Islet amyloid Polypeptide | Islets of Langerhans<br>Diabetes type II, Insulinoma |

*Non-fibrillar proteins, e.g., protein AP (amyloid P-component) excluded
**Abbreviations not explained in table:
AA = amyloid A protein;
SAA = serum amyloid A protein;
apo = apolipoprotein;
L = immomoglobulin light chain;
H = immunoglobulin heavy chain Mammal: This term includes both human and non-human mammals. Similarly, the term "subject" includes both human and veterinary subjects.

Animal: Living multicellular vertebrate organisms, a category which includes, for example, mammals and birds.

Analog, derivative or mimetic: An analog is a tetrapyrrole, or tetrapyrrole like molecule, that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in *Remington: The Science and Practice of Pharmacology*, $19^{th}$ Edition (1995), chapter 28. A derivative is a biologically active molecule derived from the base structure. A mimetic is a biomolecule that mimics the activity of another biologically active molecule. Biologically active molecules can include both chemical structures and peptides of protein entities that mimic the biological activities of the tetrapyrroles of the present invention.

Liposome: A synthetic membrane vesicle that can be used as a drug delivery vehicle. Examples of liposomes that are useful for delivery of agents to the central nervous system are shown in U.S. Pat. No. 5,576,018, and other patents and publications referenced in that patent.

The term "alkyl" refers to a cyclic, branched or straight chain alkyl group containing only carbon and hydrogen, and unless otherwise mentioned contains one to twelve carbon atoms. This term is further exemplified by groups such as methyl, ethyl, n-propyl, isobutyl, t-butyl, pentyl, pivalyl, heptyl, adamantyl, cyclopropyl, and cyclopentyl. Alkyl groups can either be unsubstituted or substituted with one or more substituents, e.g. halogen, alkyl, alkoxy, allylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

The term "lower alkyl" refers to a cyclic, branched or straight chain monovalent alkyl radical of one to seven carbon atoms. This term is further exemplified by such radicals as methyl, ethyl, n-propyl, i-propyl, n-butyl, t-butyl, i-butyl (or 2-methylpropyl), cyclopropylmethyl, i-amyl, n-amyl, hexyl and heptyl. Lower alkyl groups can also be unsubstituted or substituted, where a specific example of a substituted alkyl is 1,1-dimethyl heptyl.

The term "alkenyl" refers to a cyclic, branched, or straight chain carbon and hydrogen containing group with at least one carbon-carbon double bond. Alkyenyl groups can either be unsubstituted or substituted with one or more substituents, e.g. halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality. Specific alkenyl groups include vinyl and cyclopentenyl.

The term "alkynyl" refers to a cyclic, branched, or straight chain carbon and hydrogen containing group with at least one carbon-carbon triple bond. Alkyenyl groups can either be unsubstituted or substituted with one or more substituents, e.g. halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality. Specific alkenyl groups include propynyl and cyclopentynyl.

"Hydroxyl" refers to —OH.

"Hydroxyalkyl" refers to —R—OH, wherein R is alkylene, especially lower alkylene (for example in methylene, ethylene or propylene). A hydroxyalkyl group may be either linear or branched, such as 1-hydroxyisopropyl.

"Carbonyl containing group" refers to any subustituent containing a CO double bond. Carbonyl containing group refers to —COR where R is alkyl, lower alkyl, hydroxyl, secondary, tertiary, or quaternary amine. The term also encompasses oximes and hydrazones. Alternatively it refers to —R'COR groups wherein R is alkyl, lower alkyl, hydroxyl, secondary, tertiary, or quaternary amine and R' is alkylene, such as methylene (—CH$_2$—). Examples include —COOH, —CH$_2$COOH, —CH$_2$COOCH$_3$, —CH$_2$CONH$_2$, and CH$_2$CON(CH$_3$)$_2$.

The term "aryl" or "Ar" refers to a monovalent unsaturated aromatic carbocyclic group having a single ring (e.g. phenyl) or multiple condensed rings (e.g. naphthyl or anthryl), which can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "alkoxy" refers to a substituted or unsubstituted alkoxy, where an alkoxy has the structure —O—R, where R is substituted or unsubstituted alkyl. In an unsubstituted alkoxy, the R is an unsubstituted alkyl. The term "substituted alkoxy" refers to a group having the structure —O—R, where R is alkyl which is substituted with a non-interfering substituent. The term "arylalkoxy" refers to a group having the structure —O—R—Ar, where R is alkyl and Ar is an aromatic substituent. Arylalkoxys are a subset of substituted alkoxys. Examples of useful substituted alkoxy groups are: benzyloxy, naphthyloxy, and chlorobenzyloxy. The term "alkoxyalkyl" refers to a group having the structure —R—O—R' wherein R is alkylene, such as methylene, and R' is alkyl.

The term "aryloxy" refers to a group having the structure —O—Ar, where Ar is an aromatic group. A particular aryloxy group is phenoxy.

The term "acyl" refers to a group having the structure —OOCR, wherein R is alkyl, alkenyl, alkynyl, or aryl. A particular acyl groups is acetyl.

The term "thiol" refers to a group having the structure —R—S—H; an example is —CH$_2$CH$_2$SH.

The term "alkylthialkyl" refers to a group having the structure —R—S—R' wherein, R is alkylene, such as —CH$_2$—, and R' may be alkyl or aryl. A particular example is —CH$_2$SCH$_3$.

The term "heterocycle" refers to a monovalent saturated, unsaturated, or aromatic carbocyclic group having a single ring (e.g. morpholino, pyridyl or flryl) or multiple condensed rings (e.g. indolizinyl or benzo[b]thienyl) and having at least one heteroatom, defined as N, O, P, or S, within the ring, which can optionally be unsubstituted or substituted with, e.g. halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-_yl, or other functionality.

"Arylalkyl" refers to the groups —R—Ar and —R—HetAr, where Ar is an aryl group. HetAr is a heteroaryl group, and R is a straight-chain or branched chain aliphatic group. Example of arylaklyl groups include benzyl and furfuryl. Arylalkyl groups can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "halo" or "halide" refers to fluoro, bromo, chloro and iodo substituents.

The term "amino" refers to a chemical functionality —NR'R" where R' and R" are independently hydrogen, alkyl, or aryl. The term "quaternary amine" refers to the positively charged group (—NR'R"R'")$^+$ wherin R', R", and R'" are independently alkyl or aryl. A particular amino group is —NH$_2$. A particular quaternary amine group is —N(CH$_3$)$_3$$^+$.

The article "a" or "an" include both the singular or plural, unless the context of its use clearly indicates otherwise.

Some Tetrapyrroles Useful in the Present Invention

A tetrapyrrole is any molecule that contains four pyrrole moieties linked by covalent bridges to form a conjugated macrocycle. A pyrrole moiety is a five-membered aromatic ring structure containing a nitrogen (N) at one vertex and carbons (C) at the other four vertices. The covalent bridges may contain varying numbers of carbon and/or nitrogen atoms, for example, 0, 1, 2, or 3 atoms per bridge. Bridges may also comprise a carbonyl group. Included are derivatives where substitutions or additions alter the conjugation pattern of the molecule.

Tetrapyrroles include porphines, porphyrins (including protoporphyrins), meso-porphyrins, hydroporphyrins, azaporphyrins, anthraquinocyanines, benzoporphyrins, chlorins, deuteroporphyrins, phytoporphyrins, pyridoporphyrazines, pyrazinoporphyrazines, rhodoporphyrins, phylloporphyrins, phthalocyanines (Pc), napthalocyanines, anthracyanines, their salts, and their metal complexes. In some embodiments, the tetrapyrroles exclude some or all protoporphyrins, for example protoporphyrins such as protohemin, protohematin, or zinc protoporphyrin.

Porphyrins are macrocyclic tetrapyrrole compounds with bridges of one carbon atom, joining the pyrrole moieties. The structure of the unsubstituted porphyrin parent structure called porphine is shown below:

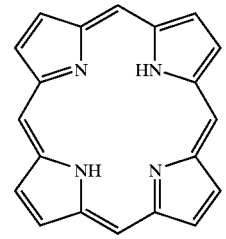

Substitution of the porphine ring may occur at both the t postitions and the meso positions as shown below.

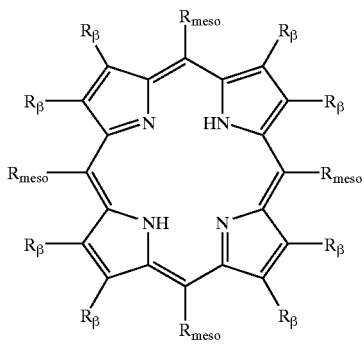

Substitution at the β and meso positions may yield symmetrical or unsymmetrical tetrapyrroles. Alkyl groups, alkenyl groups, alkynyl groups, aryl groups, aryloxy, carbonyl containing groups, heterocyclic groups, halogens, acyl groups, alkoxy groups, arylalkyl groups, hydroxyalkyl, alkoxyalkyl groups, nitro groups, sulfato groups, substituted aryl groups, substituted pyridyl groups, thiol groups, alkylthialkyl groups and hydroxyl groups are examples of groups that may occupy the β and meso positions. Subsitutions may include the fusion of cycloalkyl, cycloalkenyl, and aryl rings to the parent porphine structure, either at a pair of β positions or between a meso postition and a β position. One example of a tetrapyrrole formed from the parent porphine ring by fusion of aryl rings at a pair of β positions is tetrabenzoporphyrin, shown below.

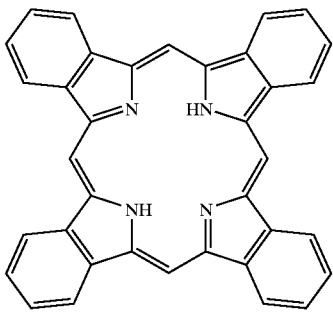

Particular examples of substituted porphyrins include the meso-substituted porphyrins, which have the general structure below:

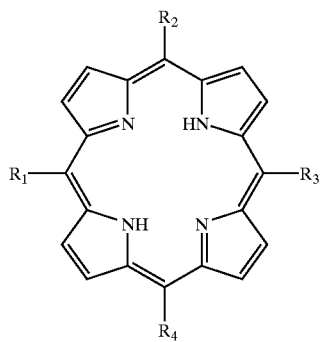

wherein $R_1$, $R_2$, $R_3$, and $R_4$ can be the same or different and are selected from the group consisting of alkyl groups, alkenyl groups, alkynyl groups, aryl groups such as phenyl, cycloalkyl groups, hydroxyalkyl groups, aryloxy groups, cartonyl groups including carboxylic acids, carhoxylic esters, carboxylic a.ides, oximes, and hydrazones, halogens, nitro groups, sulfato groups, thiol groups, alkylthioalkyl groups, secondary, tertiary, and quaternary amine groups, hydroxyl groups, methoxy groups, phosphato groups, heterocyclic groups such as 2-pyridyl, 3-pyridyl, and 4-pyridyl, halogens, acyl groups such as decanoate, alkoxy groups such as methoxy, alkoxyalkyl groups, and hydroxyl groups. Aryl groups may further be substituted with alkyl groups, carboxylate groups, including esters and amides thereof, halogens, sulfate groups, secondary, tertiary, and quaternary amine groups, hydroxyl groups, alkoxy groups, or phosphato groups. Pyridyl groups may further be N-substituted with alkyl groups, for example lower alkyl, such as C1–5 alkyl to form quaternary pyridinium ions. Alternatively, the basic pyridyl groups can be protonated at appropriate pH's to form cationic pyridinium groups.

Substituted porphyrins, wherein substituents appear at the β positions, include the deuteroporphyrins. Deuteroporphyrins are tetramethyl dipropionic acid substituted porphines, of the formula:

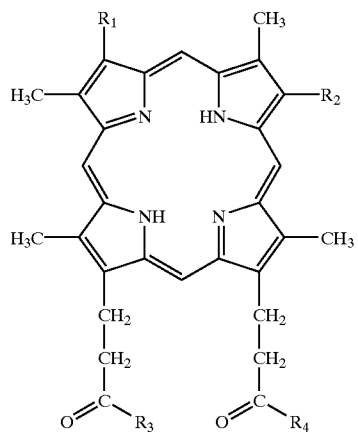

where $R_1$ and $R_2$ may be chosen independently from the group consisting of hydrogen, alkyl groups, alkenyl groups, alkynyl groups, aryl groups, carbonyl containing groups, heterocyclic groups, halogens, acyl groups, alkoxy groups, alkoxyalkyl groups, thiol groups, alkylthialkyl groups, amine groups, sulfato, phospato, and hydroxyl. $R_3$ and $R_4$ may be chosen independently from the group consisting of hydrogen, alkyl groups, amino, alkylamino groups, and hydroxyl. Some further examples of β substituted porphines are found in Dolphin, D. Ed., *The Porphynins*, Vol 1, Chap 1, pp 1–27. A particular example is deuteroporphyrin IX, wherein $R_1$ and $R_2$ are hydrogen and $R_3$ and $R_4$ are hydroxyl.

In phthalocyanines, each pyrrole ring has a six membered aromatic carbon ring fused at carbons β to the nitrogen atom of the pyrrole moiety, and the α carbons of each pyrrole moiety are joined via a single nitrogen atom bridge as shown below.

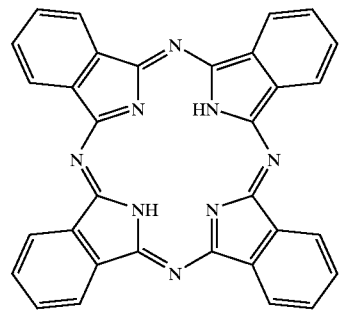

Phthalocyanines can also be substituted at any position on the outermost benzene rings as was discussed above for aryl groups of mesosubstituted porphyrins bearing such aryl groups.

In napthalocyanines the outermost benzene rings of the phthalocyanine structure are fused with yet another benzene ring to yield either a 1,2-napthalocyanine or a 2,3-napthalocyanine. The structure of 2,3-napthalocyanine, also known simply as napthalocyanine, is shown below.

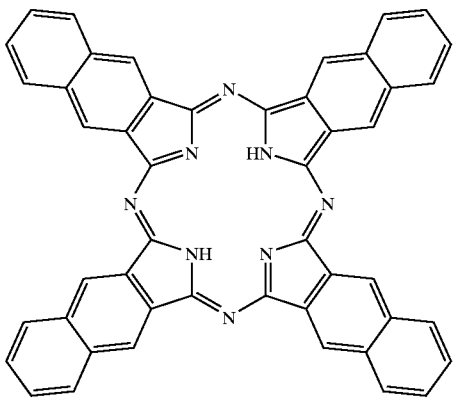

Napthalocyanines can also be substituted at any position on the outermost napthalene rings as was discussed above for aryl groups of meso-substituted porphyrins bearing such aryl groups.

In general, sulfonate salts of tetrapyrroles can readily be synthesized through sulfonation of the parent porphine ring structure and/or aromatic groups that are attached to the parent structure. Sulfonation typically yields a mixture of isomers, and the extent of sulfonation can be controlled to yield various derivatives. Other salts of the tetrapyrroles can also be synthesized, for example phosphate salts. As an example of a sulfonated tetrapyrrole, the general structure of a phthalocyanine tetrasulfonate is shown below:

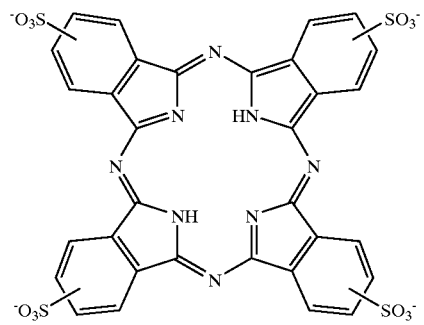

The position of the sulfato groups on each of the outer benzene rings varies, and depends upon the reaction conditions (known in the art) that are used to convert phthalocyanine to its sulfonate salts. Phthalocyanine sulfonates include phthalocyanine monosulfonate, phthalocyanine disulfonate, phthalocyanine trisulfonate (PcTrS), and phthalocyanine tetrasulfonate (PcTs), with one, two, three, or four sulfate groups on different benzene rings, respectively Complexes of tetrapyrroles are formed by replacing the central hydrogens of the porphine ring with a metal, metalloid, or a metal compound. The center nitrogens of the tetrapyrrole macrocycle, a commnon feature of the tetrapyrroles discussed above, may bond to and form complexes with virtually all metals and metalloids. At least one of the four nitrogens at the center of the tetrapyrrole macrocycle may participate in complex formation. The metal or metalloid may be in the form of an ion, such as $Fe^{3+}$, or a compound, such as VO. Metals or metalloids that form tetrapyrrole complexes include Li, Na, Mg, B, Al, Si, P, K, Ca, Sc, Ti, V, Cr, Mn, Fe, Co, Ni, Cu, Zn, Ga, Ge, As, Rb, Sr, Y, Zr, Nb, Mo, Tc, Ru, Rh, Pd, Ag, Cd, In, Sn, Sb, Cs, Ba, La, Hf, Ta, W, Re, Os, Ir, Pt, Au, Hg, Tl, Pb, Bi, Th, and the lanthanides. Included are complexes wherein the metal or metalloid is of a specific oxidation state. For example, tetrapyrroles may form complexes with both $Co^{2+}$ and $Co^{3+}$. Also included are tetrapyrrole complexes wherein the metal, metalloid, or metal compound has additional ligands. As used in this specification, the prefix "metallo" includes complexes formed with metalloids, unless specifically stated otherwise.

In certain embodiments of this invention, the tetrapyrroles do not include protoporphyrins, such as protohemin, protohematin, or zinc protoporphyrin. The general structure of protohemin ($Fe^{3+}$ protoporphyrin chloride) is shown below; protohematin has hydroxyl instead of chloride as a ligand to the central iron ion; zinc protoporphyrin has $Zn^{2+}$ at the center of the protoporhpyrin ring instead of $Fe^{3+}$:

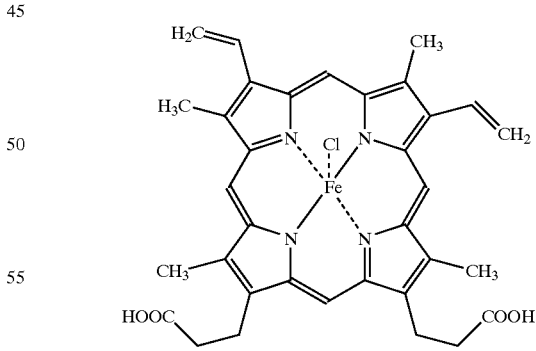

The tetrapyrrole compounds used in the examples which follow were obtained from either Porphyrin Products, Inc. (Logan, Utah) or Midcentury Chemicals (Posen, Ill.), stored according to the manufacturer's directions, and used as received.

EXAMPLE 1

Inhibition of PrP-res Formation and Immunoblot Assay for PrP-res Accumulation in ScNB Cell Cultures Scrapie infected neuroblastoma (ScNB) cells were used to study the inhibitory effect of the tetrapyrroles of the present invention in formation of PrP-res in culture. The relative amounts of PrP-res formed were measured in the presence or absence of the tetrapyrrole inhibitors.

Putative inhibitors of PrP-sen to PrP-res conversion were added to a medium containing ScNB cells seeded at 5% confluent density, and the cultures were allowed to grow to confluence over 3–4 days. The cells were then harvested, lysed with detergent and analyzed for PrP-res content by immunoblotting. The lysates were cleared of debris with a low speed centrifugation, and treated with proteinase K (PK) at a concentration of 20 µg/mL to remove PrP-sen.

The PrP-res was pelleted by ultracentrifugation, solubilized in SDS-PAGE sample buffer and run on 14% acrylamide precast gels (Novex). Proteins were electroblotted onto IMMOBILON™ membranes (Millipore) and PrP detected using a polyclonal rabbit antiserum (R30) raised against a synthetic peptide corresponding to residues 89–103 of the mouse PrP amino acid sequence and a peroxidase-conjugated goat anti-rabbit secondary antibody, as described in Caughey et al., *J. Virol.* 65:6597–6603, 1991.

The blots were developed using ECL reagents according to the manufacturer's instructions (Amersham). When 10 µM concentrations of the tetrapyrroles were added to the medium, the brightness of the 27 kD PrP-res band was greatly reduced or eliminated with many of the PcTS compounds, as compared to the control (FIG. 1A). Relative PrP-res band intensities were estimated visually by comparing autoradiographic exposure times giving equivalent band intensities.

FIG. 1B shows the concentration dependent effect of PcTS-$Fe^{3+}$ across a concentration range of 0–10,000 nM, illustrating that concentrations of at least 100 nM were effective in inhibiting the formation of PrP-res (as measured by attenuation of the 27 kD band associated with PrP-res). FIG. 1C shows the inhibitory effect of 10 µM PcTS-$Fe^{3+}$ after incubation with the medium for only 1 hour prior to treatment with PK. For all immunoblots, the primary antibody R30 was used to detect PrP-res in the PK digested cell extracts.

EXAMPLE 2

Metabolic Labeling and Immunoprecipitation of PrP-sen in ScNB Cells

This example illustrates that addition of the tetrapyrrole PcTS-$Fe^{3+}$ does not interfere with cellular protein synthesis in the ScNB cells.

The ScNB cells (25 $cm^2$ flasks) were pretreated with PcTS-$Fe^{3+}$, which was added to the culture medium either 3 days or 1 hour prior to labeling of the cells at confluence with $^{35}$S-methionine. PcTS-$Fe^{3+}$ was also maintained at the same concentration in the labeling medium. Then 5 µl aliquots of 1 ml cell lysates were run directly on the SDS-PAGE gel and the remainder of each lysate was used for the immunoprecipitation of the $^{35}$S-PrP-sen. The $^{35}$S-methionine labeling of the cells and the immunoprecipitation of $^{35}$S-PrP-sen was performed as described previously (Caughey et al., 1993, *J. Virol.* 67, 6270–6272) except that a 1 hour pulse and no chase was used for the labeling. PcTS-$Fe^{3+}$ was maintained at 10 µM in the labeling media of all but the control cells.

Little difference in the $^{35}$S-PrP-sen band intensities or the overall profile of $^{35}$S-proteins in the cells were observed. Phosphor autoradiographic quantitation of the PrP-sen bands in four experiments indicated that the 3-day and 1-hour pretreated cells had 110±30% and 113±21% (mean±SEM) inhibition of $^{35}$S-PrP-sen or untreated control cells, respectively. Moreover, none of the compounds tested in this study affected the rate of growth of the cells to confluence. Thus, the inhibition of PrP-res formation by PcTS-$Fe^{3+}$ was not due to effects on cell division, protein biosynthesis in general or the biosynthesis of PrP-sen in particular.

The autoradiograph of FIG. 2A shows that there was no significant difference between the total protein bands in the control (C), and the cells treated with PcTS-$Fe^{3+}$ for three days or one hour.

EXAMPLE 3

Cell-free Conversion Reactions

Cell free conversions were performed by exposing PrP-sen to PrP-res in the presence of guanidium (such as GdnHCl) under conditions that would be expected to form PrP-res, and the ability of the tetrapyrroles to inhibit this conversion reaction was measured by comparing the concentration of PrP-res produced in the presence and absence of the tetrapyrroles.

The PrP-res was purified from the brains of hamsters infected with the 263K strain as described in Caughey et al., 1991, *Biochemistry* 30, 7672–7680. Preparation of $^{35}$S-labeled hamster PrP-sen was carried out as described in Raymond et al., 1997, *Nature* 388, 285–288. The PrP-sen used was a recombinant PrP-sen that lacks a glycophosphatidylinositol anchor because of the introduction of a stop codon at hamster PrP codon 231 (Chesebro et al., 1993, in *Transmissible Spongiform Encephalopathies-Impact on Animal and Human Health*. ed. Brown, F;. Karger, Basel, pp. 131–140). Conversions in the presence of GdnHCl were performed as described in Raymond et al., 1997, *Nature* 388, 285–288. First PrP-res was incubated in 2.5 M GdnHCl for 1 hour at 37° C. Then the GdnHCl-treated PrP-res was mixed with $^{35}$S-labeled PrP-sen (20,000 cpm) in the presence of 1 M GdnHCl, 1.25% N-lauryl sarcosine, 5 mM acetyl pyridinium chloride, and 50 mM sodium citrate (pH 6.0).

For GdnHCl-free conversions, PrP-res was diluted to 50 ng/µl with water and sonicated briefly. Then 100 ng of PrP-res was mixed with $^{35}$S-labeled PrP-sen (20,000 cpm) in a total volume of 20 µl which also contained 200 mM KCl, 5 mM $MgCl_2$, 0.625% N-lauryl sarcosine, and 50 mM sodium citrate (pH 6.0). Conversion reaction mixtures were incubated at 37° for 2 days. Nine-tenths of reaction mixture was treated with 20 µg/ml of PK [50 mM Tris-HCl (pH 8.0), 150 mM NaCl, in 100 µl] for 1 hour at 37° C. to degrade the PrP-sen but not the PrP-res. Digestion by PK was stopped by adding Pefabloc™ (Boehringer Mannheim) to 2 mM. Thyroglobulin (20 µg) was added as a carrier. The remaining one-tenth of the reaction mixture was analyzed without PK treatment. Methanol precipitates of the proteins were subjected to SDS-PAGE using 14% acrylamide precast gels (Novex). Radioactive proteins were visualized and quantified by using a Storm PHOSPHORIMAGER™ instrument (Molecular Dynamics).

Inhibition of cell-free conversion of PrP-sen to PrP-res by PcTS-$Fe^{3+}$ and PcTS-$Al^{3+}$ under GdnHCl-free conditions are shown in FIGS. 3A and 3B. The open and closed triangles represent monoglycosylated and unglycosylated $^{35}$S-PrP-res respectively, without PK treatment. The open and closed circles represent monoglycosylated and unglycosylated $^{35}$S-PrP-res respectively, after PK digestion. Molecular mass markers are designated in kD to the right side of the panels.

The results of cell-free conversion assays with PcTS-$Fe^{3+}$ and PcTS-$Al^{3+}$ are shown in FIGS. 3D and 3E. These graphs illustrate that PcTS-$Fe^{3+}$ is more effective than PcTS-$Al^{3+}$ both in the presence of GdnHCl (FIG. 3D) and in the GdnHCl-free (FIG. 3E) assay. The assay was effective either with or without GdnHCl.

EXAMPLE 4

Inhibition of PrP-res Formation by Phthalocyanine (Pc) Sulfonates in ScNB Cells Pc sulfonates were added to the medium of scrapie infected neuroblastoma (ScNB) cells seeded at 5% confluent density and the cultures were allowed to grow to confluence over 3–4 days. The cells were then harvested and analyzed for PrP-res content by immunoblotting, to look for the disappearance of protein bands associated with PrP-res. Each Pc sulfonate, at a concentration 10 µg/ml (about 10 µM), reduced the level of PrP-res detected, compared to the percentage of PrP-res present in control trials without the Pc. Metal-free, $Fe^{3+}$, Mn3+, $Co^{3+}$, $Cu^{2+}$, $Ni^{2+}$, and VO complexes were better inhibitors than the $Co^{2+}$, $Zn^{2+}$ or $Al^{3+}$ complexes. Further testing of selected Pc sulfonates at lower concentrations allowed the estimation of the indicated $IC_{50}$ values, with the lowest being the metal-free and PcTS-$Fe^{3+}$ with $IC_{50}$ values of <1 µM.

Table 2 shows the relative inhibitory effect of various phthalocyanine sulfonates (either metal-free, or complexed with various metal ions). PrP-res band intensities were measured as the mean percent of band intensity (±SD) relative to that produced by untreated control ScNB cells (% control PrP-res). Inhibition of conversion to the protease resistant form PrP-res can be determined by the intensity between the PK-resistant 35S labelled bands that are approximately 5–10 kDa lower in molecular mass than the non-digested 35S-PrP-sen as quantitated by phosphor autoradiographic image analysis. All Pcs were tested at 10 µM, and a few at even lower concentrations, to estimate the concentration giving 50% inhibition of PrP-res formation relative to control ($IC_{50}$).

In Table 2, PcTS and PcTrS designate phthalocyanine compounds with four and three sulfonic acid groups per molecule, respectively. One sulfonic acid group is found on each peripheral six-membered ring; variation in site of substitution results in a mixture of isomers. Metal complexes are indicated by a metal ion formula following the compound abbreviation. In these cases, a greater than 80% drop in the $^{35}$S-PrP-res formation was observed between 10-fold dilutions of the inhibitor. The $IC_{50}$ is the concentration half-way between the 10-fold dilutions tested, but the actual value could be ±50% of that value.

TABLE 2

Phthalocyanine Inhibition of PrP-res Formation

| Compound Designation | M | % control PrP-res (at 10 µg Pc/ml) | IC50 (µM) |
|---|---|---|---|
| PcTS |  | <3 | 0.5[a] |
| PcTS-$Fe^{3+}$ | $Fe^{3+}$ | <2 | 0.9 ± 0.2 |
| PcTS-$Mn^{3+}$ | $Mn^{3+}$ | <2 |  |
| PcTS-$Co^{3+}$ | $Co^{3+}$ | <2 |  |
| PcTS-$Co^{2+}$ | $Co^{2+}$ | 19 ± 9 |  |
| PcTS-$Cu^{2+}$ | $Cu^{2+}$ | <3 |  |
| PcTS-$Ni^{2+}$ | $Ni^{2+}$ | <3 |  |
| PcTS-$Zn^{2+}$ | $Zn^{2+}$ | 13 ± 2 | ~5[a] |
| PcTS-VO | VO | <2 |  |
| PcTS-$Al^{3+}$ | $Al^{3+}$ | 75 ± 25 | >10 |
| PcTrS-$Al^{3+}$ | $Al^{3+}$ | 38 ± 18 |  |
| PcTrS-$Zn^{2+}$ | $Zn^{2+}$ | 8 ± 5 |  |

[a]In these cases, a >80% drop in the $^{35}$S-PrP-res formation was observed between the 10-fold dilutions of the inhibitor; we report the $IC_{50}$ as the concentration half-way between the 10-fold dilutions tested, but the actual value could be ±50% of that valued.

To control for the possibility that these effects were due to artifactual interference with the detection of PrP-res rather than an inhibition of PrP-res accumulation in the cells, one of the most effective inhibitors, PcTS-$Fe^{3+}$, was added at 10 µM (about 10-fold higher concentration than the $IC_{50}$) to cell lysates before the addition of PK and further processing for the detection of PrP-res. No effect on the PrP-res immunoblots band intensity was observed in comparison to untreated control cell lysates (FIG. 2C), indicating that the PcTS-$Fe^{3+}$ did not interfere with PrP-res detection.

EXAMPLE 5

Inhibition of PrP-res Formation by Deuteroporphyrins (DP) in ScNB Cells

Using the assays described in Example 4, the inhibitory effect of deuteroporphyrins on the conversion of PrP-sen to PrP-res was determined. As illustrated in Table 3, the deuteroporphyrins $DP(SO_3^-)_2$ and $DP(SO_3^-)_2Fe^{3+}$ were shown to be about equally effective in reducing PrP-res formation at concentrations of 10 μg/ml (about 12 μM). Converting the propionate groups to uncharged methyl esters as in $DP(SO_3^-)_2Me_2$ resulted in less inhibition. Inhibitory potency was retained by molecules containing glycols in place of the sulfonates, and the $Fe^{3+}$ complex of $DP(glycol)_2$ was a better inhibitor than the metal-free compound.

Table 3 shows the relative inhibitory effect of various deuteroporphyrins, and the identity of the various substituents that comprise $R_1$ and $R_2$, as defined above for deuteroporphyrins. Metal complexes of the deuteroporhyrins are indicated by the addition of the metal ion after the abbreviation. As in the previous example, band intensities were analyzed for the mean intensity relative to that produced by untreated control ScNB cells, and $IC_{50}$ was also determined as in the last example.

EXAMPLE 6

Inhibition of PrP-res Formation by Mesoporphyrins in ScNB Cells

Table 4 shows the relative inhibitory effect of various meso-substituted porphyrins. For the tetraphenyl porphyrin derivatives of the table, the portion of the compound abbreviation in parentheses indicates the position and identity of substituents of the phenyl groups found at all four meso positions of the porphine ring. For the tetrapyridyl porphyrin derivatives, the portion of the abbreviation in parentheses indicates whether the pyridyl groups found at all four meso positions of the porphine ring are connected to the porphine ring at the 2, 3, or 4 position of the pyridine ring. Also, within the parentheses of the tetrapyridyl porphyrin abbreviations, N-Me indicates N-methylation of the pyridyl groups to yield cationic quaternary pyridinium groups.

Among the metal-free tetraphenyl porphines (TPhPs), the presence of the positively-charged quaternary amine groups of $T(Ph4-NMe_3^+)P$ resulted in more effective inhibition than either of the negatively-charged carboxylate and sulfonate groups of $T(Ph-4-COOH)P$ and $T(Ph-4-SO_3^-)P$, respectively. Insertion of $Fe^{3+}$ into $T(Ph-4-COOH)P$ increased the inhibition significantly, but an increase was not evident with insertion of either $Fe^{3+}$ or $Mn^{3+}$ into $T(Ph4-SO_3^-)P$. The metal-free and $Fe^{3+}$ complex of $T(Ph4-NMe_3^+)$ had comparable $IC_{50}$ values.

TABLE 3

Deuteroporphyrin Inhibition of PrP-res Formation

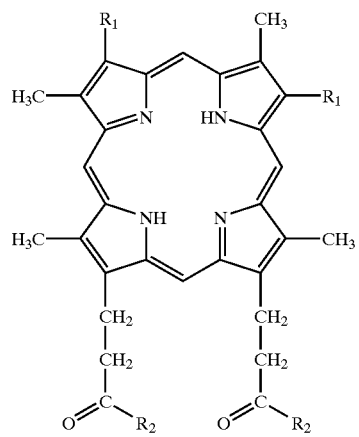

Metal-free deuteroporphyrin

| Compound Designation | $R_1$ | $R_2$ | M | % control PrP-res (at 10 μg DP/ml) | $IC_{50}$ (μM) |
| --- | --- | --- | --- | --- | --- |
| $DP(SO_3^-)_2$ | $-SO_3^-$ | $-O^-$ | | $6 \pm 0^a$ | |
| $DP(SO_3^-)_2 ME_2$ | $-SO_3^-$ | $-OCH_3$ | | $37 \pm 12$ | |
| $DP(SO_3^-)_2Fe^{3+}$ | $-SO_3^-$ | $-O^-$ | $Fe^{3+}$ | $6 \pm 1$ | $7.5 \pm 1$ |
| $DP(glycol)_2$ | H H<br>—C —CH<br>O O<br>H H | $-O^-$ | | $25 \pm 0^a$ | |
| $DP(glycol)_2Fe^{3+}$ | H H<br>—C —CH<br>O O<br>H H | $-O^-$ | $Fe^{3+}$ | $1 \pm 2$ | $1.0 \pm 1$ |

[a] In these cases, no difference in PrP-res immunblot signal intensity could be discerned visually between replicates, however, with the autoradiographic methodology used, it was difficult to discriminate differences of ±5%.

The tetra-pyridyl porphyrins (TPyPs) studied included those with positively-charged N-methyl pyrididyl groups and T(4-Py)P. The latter unmethylated compound contains basic pyridine nitrogens that can become positively charged on protonation at appropriately low pHs. At 10 μg/ml (~10 μM), T(4-Py)P was a somewhat more effective inhibitor than either T(N-Me-4-Py)P or T(N-Me-3-Py)P, but less effective than T(N-Me-2-Py)P. Conversion of T(N-Me4-Py)P to a metal-complex with $Fe^{3+}$, $Cu^{2+}$, $Ni^{2+}$ or $Zn^{2+}$ resulted in a more effective inhibitor.

The tetraphenyl and tetrapyridinyl derivatives all inhibited formation of PrP-res, but inhibition was better with para and ortho substitutions than with a meta substitution.

TABLE 4

Inhibition of PrP-res Formation by Meso-Porphyrins

| Compound Designation | $R_1$—$R_4$ | M | % control PrP-res (at 10 μg TSP/ml) | $IC_{50}$ (μM) |
|---|---|---|---|---|
| T(Ph-4-$SO_3^-$)P |  |  | 44 ± 31 | ~5[b] |
| T(Ph-4-$SO_3^-$)P—$Fe^{3+}$ | —⌬—$SO_3^-$ | $Fe^{3+}$ | 5 ± 2 | 7 ± 1 |
| T(Ph-4-$SO_3^-$)P—$Mn^{3+}$ |  | $Mn^{3+}$ | 75 ± 35 |  |
| T(Ph-4-COOH)P |  |  | 50 ± 0[a] | ~5[b] |
| T(Ph-4-COOH)P—$Fe^{3+}$ | —⌬—$COO^-$ | $Fe^{3+}$ | <3 |  |
| T(Ph-4-$NMe_3^+$)P |  |  | <3 | 5 ± 0.8 |
| T(Ph-4-$NME_3^+$)P—$Fe^{3+}$ | —⌬—$N(CH_3)_3^+$ | $Fe^{3+}$ | <2 | 6.5 ± 1.5 |
| T(4-Py)P | —⌬N |  | 12 ± 0[a] |  |
| T(N-Me-4-Py)P |  |  | 50 ± 0[a] |  |
| T(N-Me-4-Py)P—$Fe^{3+}$ |  | $Fe^{3+}$ | <3 | 0.5 ± 0.3 |
| T(N-Me-4-Py)P—$Cu^{2+}$ | —⌬$N^+$—$CH_3$ | $Cu^{2+}$ | <3 |  |
| T(N-Me-4-Py)P—$Ni^{2+}$ |  | $Ni^{2+}$ | <3 |  |
| T(N-Me-4-Py)P—$Zn^{2+}$ |  | $Zn^{2+}$ | <2 |  |
| T(N-Me-3-Py)P | —⌬(N$^+$CH_3) |  | 50 ± 0[a] |  |
| T(N-Me-2-Py)P | —⌬(N$^+$CH_3) |  | 4 ± 3 | ~5[b] |

[a]In these cases, no difference in PrP-res immunoblot signal intensity could be discerned visually between replicates, however, with the autoradiographic methodology used, it was difficult to discriminate difference of ~±5%.
[b]In these cases, a >80% drop in the $^{35}$S-PrP-res formation was observed between 10-fold dilutions of the inhibitor; we report the $IC_{50}$ as the concentration half-way between the 10-fold dilutions tested, but the actual value could be ~±50% of that value.

EXAMLPE 7

Inhibition of PrP-res Formation in a Cell-free System

The effect of tetrapyrroles on PrP-res formation was examined in the highly specific cell-free conversion reaction set forth in Example 3. PrP-res isolated from scrapie-infected hamster brain tissue was used to induce the conversion of immunoprecipitated hamster $^{35}$S-PrP-sen to $^{35}$S-PrP-res. Under two sets of reaction conditions PcTS-Fe$^{3+}$ and PcTS-Al$^{3+}$ inhibited $^{35}$S-PrP-res formation; in each case, the PcTS-Fe$^{3+}$ had an IC$_{50}$ (0.4 $\mu$M) that was 8-fold lower than that of PcTS-Al$^{3+}$. However, there was no apparent reduction in the PK-resistance and immunoblot detection of the input PrP-res by either compound. Additional tests with 10 $\mu$g/ml tetrapyrrole indicated that metal-free PcTS, DP(glycol)$_2$Fe$^{3+}$ and the metal-free DP(glycol)$_2$ reduced conversion to 0±0%, 3±1%, and 71±16% of control (mean□SD), respectively. Meso-tetrasubstituted porphyrins with positively charged substituents were not significantly inhibitory [T(Ph-4NMe$_3^+$)P, T(Ph-4-NMe$_3^+$)P—Fe$^{3+}$, T(N-Me-4-Py)P—Fe$^{3+}$ and T(N-Me-2-Py)P] or were weakly inhibitory T(N-Me4-Py)P (66±18% of control). Thus, with the exception of the tetrapyrroles with positively charged substituents, a variety of tetrapyrroles that inhibited PrP-res formation in the ScNB cells also inhibited the cell-free system reaction.

EXAMPLE 8

Tetrapyrrole Derivatives

The tetrapyrroles of the present invention include a wide variety of compounds that are useful to inhibit conversion of PrP-sen to PrP-res, or in inhibiting or preventing the development of amyloidogenic diseases.

Examples of substituted porphyrins are porphyrins that are substituted on the pyrrole ring, β to the pyrrole nitrogen, with carbonyls (—COR, particularly where R is H, or alkyl, such as C$_{1-5}$ alkyl, or a substituted or unsubstituted aromatic ring, such as phenyl or substituted phenyl, and carbonyl derivatives such as oximes and hydrazones); hydroxyallyl groups (particularly C$_{1-5}$) that are either monohydroxy (as in —CH$_2$OH, —CHOHCH$_3$, —CHOHR, —CH$_2$CH$_2$OH) or polyhydroxy (as in —CHOHCH$_2$OH, —CHOHCH$_2$CH$_2$OH and —CHOHCHOHCH$_2$OH); alkoxyalkyl groups (particularly groups derived from ethers,such as the groups —CH$_2$OCH$_3$, —CH$_2$CH$_2$OCH$_3$, and —CHOCH$_3$CH$_2$OCH$_3$); carboxylate groups (as in —CO$_2$H, —CH$_2$COOH, —CH$_2$CH$_2$COOH, and 2-carboxylic cyclopropyl) and carboxylate ester and amide groups as in —COOR, —CONR, and CONHCH$_2$COR, where R may be H or lower C$_{1-5}$ alkyl); halogen (particularly bromo or chloro); alkyl (particularly C$_{15}$ alkyl as in —CH$_3$, —CH$_2$CH$_3$, and —CH$_2$CH$_2$CH$_3$); or alkylthioalkyl and mercapto groups as in -R$_1$SR$_2$, where R$_1$ is C1–5 alkylene and R$_2$ is C1–5 alkyl or hydrogen (in the case of a mercapto derivative).

Examples of substituted meso-porphines are phorphines having substitutions such as nitro, alkyl(particularly lower alkyl) or aromatic groups (including substituted aromatic groups).

In addition to the metallocomplexes discussed above, additional metal complexes may be formed with Ga, Ag, Pd, Mg, Cd, and Sr. In addition to the heme derivatives already discussed, the tetrapyrroles can be related tetrapyrrole pigments, such as chlorophyll a, or chlorin e6 or purpurin.

In addition to the cyclic tetrapyrroles, linear tetrapyrroles such as bilirubin, biliverdin and derivatives may also be used.

EXAMPLE 9

Pharmaceutical Compositions

The invention provides pharmaceutical compositions of the inhibitory compounds that are useful as therapeutic agents when constituted with the appropriate carriers or diluents. Although one mode of administration of the compositions would be directly into the CNS where they can interfere with the formation of PrPres in the brain, such direct injection into the CNS is not necessary with many of these compositions because they are believed to effectively penetrate the blood brain barrier. Hence intravenous, intramuscular or other parenteral administration are also contemplated to interfere with PrPres formation both inside and outside the CNS. It is postulated that prion diseases have an early stage in which the infectious agent acts primarily in the lymphoreticular system (such as the spleen and lymph nodes), hence peripheral administration of the tetrapyrroles could act outside the CNS to inhibit progression of the disease. Oral administration is possible, as are suppositories, retrograde axoplasmic transport into the brain (from the olfactory bulb) via inhalation ocular administration (for example in the form of eye drops).

Any of the common pharmaceutical carriers, such as sterile saline solution or sesame oil, can be used. Routes of parenteral administration include, but are not limited to, subcutaneous (sq), intracranial ventricular (icv), intrathecal (it), intravenous (iv), intramuscular (im), topical ophthalmic, subconjunctival, nasal, aural and transdermal. Peptides of the invention may be administered sq, iv or im in any conventional medium for intravenous injection, such as an aqueous saline or oil medium. The medium may also contain conventional pharmaceutical adjunct materials such as, for example, pharmaceutically acceptable salts to adjust the osmotic pressure, buffers, preservatives and the like. Among the preferred media are normal saline and sesame oil.

Embodiments of the invention comprising medicaments can be prepared with conventional pharmaceutically acceptable carriers, adjuvants and counterions as would be known to those of skill in the art. The medicaments are preferably in the form of a unit dose in solid, semi-solid and liquid dosage forms such as tablets, pills, powders, liquid solutions or suspensions, and injectable and infusible solutions, for example a unit dose vial. Effective dosage ranges included in the unit dose container can readily be determined from the effective concentrations shown in dose response curves, or similar curves generated for variants, analogs, mimetics, etc.

The pharmaceutical compositions may also be administered as intranasal inhalants, for example in pharmaceutical aerosols utilizing solutions, suspensions, emulsions, powders and semisolid preparations of the type more filly described in *Remington: The Science and Practice of Pharmacy* (19$^{th}$ Edition, 1995) in chapter 95. A particular inhalant form is a metered dose inhalant containing the active ingredient, in a suspension or a dispersing agent (such as sorbitan trioleate, oleyl alcohol, oleic acid, or lecithin, and a propellant such as 12/11 or 12/114).

Therapeutically effective doses of the compounds of the present invention can be determined by one of skill in the art, with a goal of achieving tissue concentrations that are at least as high as the IC$_{50}$ of each drug tested in the foregoing examples. The low toxicity of the compound makes it possible to administer high doses, for example 100 mg/kg, although doses of 10 mg/kg, 20 mg/kg, 30 mg/kg or more are contemplated.

The pharmaceutical compositions can be used in the treatment of a large number of amyloidogenic diseases, including the following: TSE, AD, hereditary cerebral hemorrhage with amyloidosis Icelandic type (HCHWA-I), hereditary cerebral hemorrhage with amyloidosis Dutch-type (HCHWA-D), familial Mediterranean fever, familial amyloid nephropathy with urticaria and deafness (Muckle-Wells syndrome), myeloma or macroblobulinemia-associated idopathy associated with amyloid, familial amyloid polyneuropathy (Portuguese), familial amyloid cardiomyopathy (Danish), systemic senile amyloidosis, familial polyneuropathy, familial amyloidosis (Finnish), GSS, medullary carcinoma of the thyroid, isolated atrial amyloid, diabetes type II (with amyloid in the islets of Langerhans), and insulinoma. Many of these conditions are associated with deposition of PrP-res.

In a particular aspect of the invention, the compounds and compositions are useful in treating, preventing and/or inhibiting conditions associated with plaques or amyloid deposits in the CNS of an animal. In another form of the invention, the method is useful against formation of amyloid plaques, particularly plaques associated with PrP-res formation, for example in the heart, liver, spleen, kidney, pancreas, brain, lungs and muscles. For example, the method could be used in the treatment of diabetes mellitus type 11, where amyloid plaques occur in the pancreas. Alternatively, the condition to be treated are associated with deposition of a variant form of cystatin-C, such as HCHWA-I, or a form of amyloid precursor protein (APP), such as AD or HCHWA-D.

Another aspect of the invention is a method of treating a mammal, such as a human, having a condition associated with overproduction of PrP-res. In this aspect of the invention, the affected mammal is identified and treated with the tetrapyrrole.

Another aspect of the invention is a method of inhibiting the transformation of PrP-sen to PrP-res in a tissue culture sample containing PrP-sen, under conditions that would otherwise be expected to transform PrP-sen to PrP-res. In this aspect of the invention, a tetrapyrrole, or one of the specific tetrapyrroles described herein, or a salt or derivative thereof, is supplied to the tissue culture in an amount sufficient to interfere with PrP-res formation.

Other examples of disease and treatments of diseases associated with amyloid formation are disclosed in U.S. Pat. No. 5,276,059, which is incorporated by reference.

EXAMPLE 10

Animal Studies

Transgenic mice overexpressing the hamster PrP gene are used for in vivo TSE studies, to demonstrate the effectiveness of the tetrapyrroles in the inhibition of progression of TSE in an animal. These transgenic mice are susceptible to hamster scrapie, and have short incubation periods before the development of disease, which make them quite useful animal models. The different tetrapyrrole compounds are tested in doses of 3 to 20 mg/kg per dose, either alone or in combination with other tetrapyrroles. This dose is well below the expected toxicity of non-photoreactive tetrapyrroles that do not act as photosensitizers (and therefore would not be important in photodynamic therapy).

A first group of the animals is inoculated with the scrapie agent by administering a 50 µL dose of 0.1% scrapie-infected hamster brain homogenate intraperitoneally (ip) while under metafane anesthesia, and given the tetrapyrrole compound (by ip injection of a 3–20 mg/kg dose) on the same day. The same dosage of tetrapyrrole is administered three times a week for four weeks. Other groups of animals are inoculated with the scrapie agent, but tetrapyrrole treatment is not initiated until 28, 56, or 70 Dpi, and then is given 3 times a week until the onset of clinical scrapie. Another group of animals is inoculated with hamster scrapie only, and given no tetrapyrrole treatment. A final group of animals is not inoculated with the scrapie agent, but is given the tetrapyrrole compound.

Onset of clinical scrapie is determined by the development of ataxia and somnolence over a period of 2–3 weeks. To confirm the diagnosis of scrapie, brain and spleen are removed and analyzed by Western blot using the hamster PrP-specific antibody 3F4 which is a specific binding agent for PrP-res.

Figure 4:
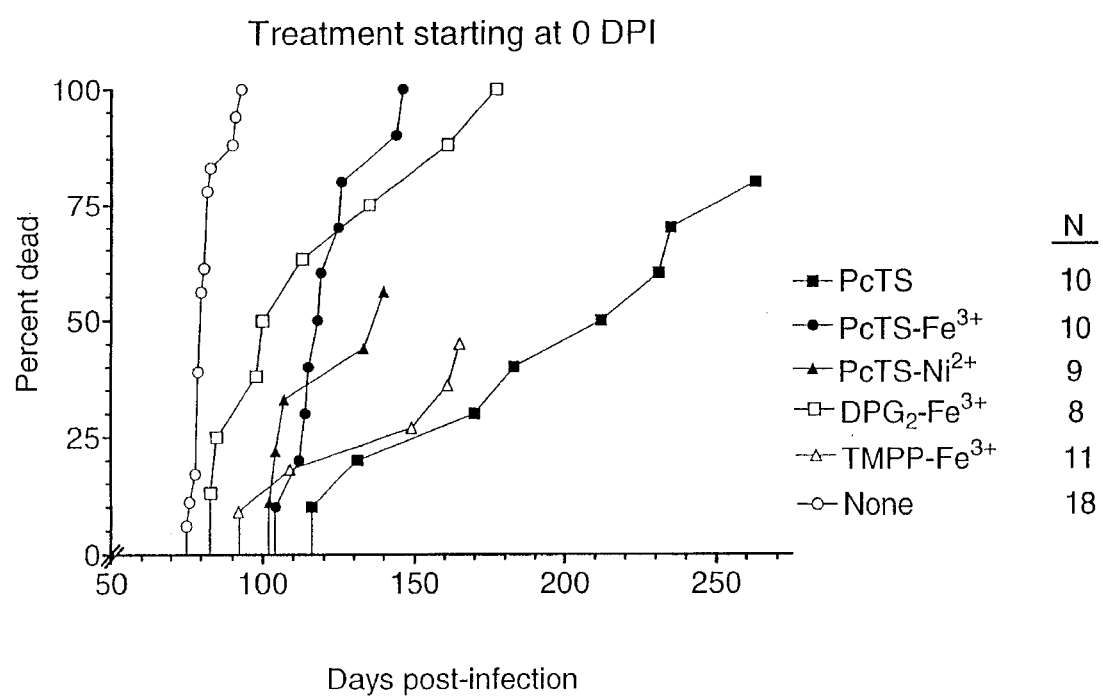
FIG. 4 shows how early treatment of scrapie-infected mice with porphyrins and pthalocyanines significantly increases survival. Days to death of hamster 293K-infected Tg7 mice, are shown, with and without treatment. Treatment was three times a week at the dosages given in Example 11. Individual data points represent the percent dead of the total number of mice for that group and may include more than one mouse. Untreated animals represent data pooled from two separate experiments. The legend is shown on the right and the number of mice is indicated under N. TMPP is tetramethylpyridylporphyrin and $DPG_2$ is the diglycol derivative of deuteroporphyrin.

In order to determine if porphyrins and phthalocyanines which inhibit PrP-res formation in vitro also inhibit TSE disease in vivo, transgenic mice over-expressing the hamster PrP-sen (Tg7) were infected IP (intraperitoneally) with 0.05 ml of a 1% hamster 263K scrapie brain homogenate. Starting on the day of infection (0 Dpi), animals were injected IP three times a week over four weeks with each of the five different tetrapyrroles. For each treatment, the dose given was 5 mg/kg PcTS, 30 mg/kg PcTS-$Fe^{3+}$ or DPG2-$Fe^{3+}$, and 10 mg/kg PcTS-$Ni^{2+}$ or TMPP-$Fe^{3+}$. Since DPG2-$Fe^{3+}$ was dissolved in 100% DMSO, a group of infected animals was treated with 100% DMSO IP using the same treatment regimen to control for any effect of DMSO on disease progression. Animals were monitored for clinical signs and sacrificed when in the terminal phases of disease Every compound tested significantly increased mean survival times when compared to untreated controls (FIG. 4). Treatment with either PcTS-$Fe^{3+}$ or DPG2-$Fe^{3+}$ increased mean survival times by 40 and 37 days respectively. The effect of DPG2-$Fe^{3+}$ was not due to the DMSO used as a diluent because infected animals treated IP with DMSO alone were significantly different from animals treated with DMSO plus DPG2-$Fe^{3+}$ (mean time to death of 84±3 days vs. 119±12.5 days). PcTS-$Ni^{2+}$ and TMPP-$Fe^{3+}$ have also been shown to increase survival times by a minimum of 35 and 53 days respectively. PcTS was the most effective compound with 60% of the animals surviving a minimum of 200 days, approximately 120 days longer than untreated controls. A second experiment with PcTS showed similar results (80% survivors at >170 Dpi, data not shown). The data demonstrate that porphyrins and phthalocyanines can dramatically inhibit TSE disease pathogenesis and thus represent an effective new type of anti-TSE drug.

In some models of scrapie, peripheral replication of infectivity in the spleen is important during the first 1–2 weeks following IP infection, particularly if the dose of infectious agent is low. The intensely colored porphyrins and phthalocyanines were visually detectable in the peritoneal cavity long after treatment had ended. For example, PcTS could be detected in the spleen at least 8 months after treatment had stopped, demonstrating that it was stably maintained in the periphery. Use of liposomal preparations of the compounds may increase the amount of the compounds crossing the blood brain barrier.

In human TSE such as CJD, where diagnosis of the disease is performed after the onset of clinical symptoms, any treatmentis ideally effective late in the infectious process. In order to determine if PcTS, PcTS-$Fe^{3+}$, or DPG2-

$Fe^{3+}$ inhibited disease progression during the later stages of infection, treatment of infected animals was begun at either 28 or 56 days post-infection. When treatment was started at 28 Dpi, PcTS and DPG2-$Fe^{3+}$ increased survival times by one week. For all the compounds, treatment early during the pathogenic process delayed disease most effectively, indicating they would be particularly useful prophylactically.

EXAMPLE 11

Prophylactic Administration of Tetrapyrroles to Prevent Onset of TSE Diseases

Humans with the knowledge that they have been or may be exposed to a TSE disease can be administered tetrapyrroles in amounts that achieve micromolar (10–100 μM, for example) concentrations in vivo. Humans with occupational exposure to TSE (such as neurosurgeons or persons who work with potentially infected animal tissue) can routinely take dosages of the compounds to provide protection from transmission.

Cows, sheep, deer, elk and other animals that are able to contract a TSE disease can be administered tetrapyrroles prophylactically to halt the spread of the disease. In one embodiment, the tetrapyrroles are administered to such animals by incorporating the tetrapyrroles into salt blocks at a concentration sufficient to achieve micromolar (10–100 μM, for example) tissue concentrations in vivo. Such salt blocks can be located, as an example, in areas previously grazed by scrapie infected sheep. Since animals grazing the same area are prone to contracting the disease for up to ten years after the initial infection, a prophylactic administration to prevent transmission is valuable. Cattle fed animal protein can be fed tetrapyrroles along with their feed or in salt blocks, at concentrations sufficient to achieve micromolar (10–100 μM, for example) concentrations in vivo.

EXAMPLE 12

Intracerebral, Intrathecal or Intraventricular Administration

Direct intracerebral injection of the drug is possible, or delivery can be accomplished by sustained delivery reservoirs or pumps that deliver a preselected concentration of the drug to areas of the brain being treated. Direct CNS delivery can be directed particularly to areas of the brain that are found to be affected on an MRI scan, or delivered to areas of the brain known to be affected by the particular strain of TSE being treated. In a human, conventional lumbar puncture with a spinal needle can be used to access the epidural or intrathecal space. In a human, icv injections can be performed using MRI guided stereotactic procedures.

The tetrapyrroles of the present invention inhibit PrP-res formation in both mouse ScNB cells and the hamster PrP cell-free conversion system. The ScNB cell experiments indicated that this inhibition occurred without apparent cytotoxicity or effects on the rate of PrP-sen biosynthesis.

Congo Red and most of the other known polyanionic inhibitors of PrP-res formation are sulfonated or sulfated. Surprisingly, however, the sulfonates or other anionic groups were not required for inhibition by the porphyrins. Indeed, porphyrins with neutral glycol, or even cationic, substituents were effective inhibitors. This aspect of the porphyrins stands in contrast to the polysulfated glycans which are ineffective when the sulfates are removed or substituted with cationic groups.

The inhibitory compounds of the present invention are known to be relatively non-toxic, and well tolerated in animals. In particular, PcTS-$Al^{3+}$, PcTrS-$Al^{3+}$, T(N-Me-4-Py)P—$Fe^{3+}$, T(Ph4-$SO_3^-$)P and T(Ph4-$SO_3^-$)P—$Fe^{3+}$ have been reported to be well tolerated.

The ability to penetrate the blood brain barrier is expected to be particularly beneficial for the treatment of disease in the CNS. Previous reports have shown that tetrapyrroles (for example PcTS-$Al^{3+}$ and several DP analogs) do cross the blood-brain barrier. The intrinsic lipophilicity of tetrapyrroles favors effective delivery of tetrapyrroles to the brain. However, even in the absence of delivery to the CNS, the inhibitors of the present invention are useful for preventing PrP-res formation outside the CNS (for example in the lymphoreticular system), and perhaps preventing spread of disease to the CNS.

The above examples are provided by way of illustration only and are in no way intended to limit the scope of the invention. One of skill in the art will understand that the invention may be modified in various ways without departing from the spirit or principle of the invention. We claim all such modifications.

We claim:

1. A method for inhibiting progression of an amyloidogenic disease in an animal comprising administering a therapeutically effective amount of a tetrapyrrole to the animal, the amyloidogenic disease being a disease in which the amyloid protein is AA, AL, AH, ATTR, AapoAI, Agel, Acys, $AB_2$, Ascr, Acal, AANF or ALAPP.

2. The method of claim 1, wherein the amyloidogenic disease is a disease in which inhibiting conversion of PrP-sen to PrP-res inhibits progression of the disease.

3. The method of claim 2 wherein the disease is a transmissible spongiform encephalopathy.

4. The method of claim 1 wherein the disease is characterized by pathological formation of amyloid deposits.

5. The method of claim 1 wherein the disease is Type 2 diabetes.

6. The method of claim 1 wherein the tetrapyrrole is selected from the group consisting of a porphine, a porphyrin, and a phthalocyanine.

7. The method of claim 1, wherein the tetrapyrrole is not protohemin, protohematin, or zinc protoporphyrin.

8. The miethod of claim 6, wherein te tetrapyrrole is selected from the group of a deuteroporphynn, a meso-substituted potphine, and a phthalocyanina.

9. The method of claim 6, wherin the animal has a disease in which inhibiting conversion of PrP-sen to Pr-Pes in an animal inhibits or prevents progession of the disease.

10. The method of claim 9, wherein the animal has a transmissible spongiform encephalopathy.

11. The method of claim 10, wherein the tetrapyrrole is not protohemin, protohematin, or zinc protoporphyrin.

12. The method of claim 8, wherein the tetrapyrrole is a phthalocyanine.

13. The method of claim 12, wherein the tetrapyrrole is a phthalocyanine sulfonate.

14. The method of claim 13, wherein the tetrapyrrole is a phthalocyanine monosulfonate, disulfonate, trisulfonate or tetrasulfonate.

15. The method of claim 13, wherein the tetrapyrrole is a metallophthalocyanine.

16. The method of claim 16, wherein the tetrapyrrole is a metallophthalocyanine containing a transition metal.

17. The method of claim 16, wherein the metal is selected from the group of iron, manganese, cobalt, nickel, zinc, vanadium, and aluminum.

18. The method of claim 17, wherein the metal is an ion selected from the group of $Fe^{3+}$, $Mn^{3+}$, $Co^{3+}$, $Cu^{2+}$, $Ni^{2+}$, $Zn^{2+}$, $Co^{2+}$, VO and $Al^{3+}$.

19. The method of claim 18, wherein the metal is an ion selected from the group of $Fe^{3+}$, $Mn^{3+}$, $Co^{3+}$, $Cu^{2+}$, $Ni^{2+}$, VO, and $Zn^2+$.

20. The method of claim 12 wherein the tetrapyrrole is a tetrasulfonylphthalocyanine (PcTs).

21. The method of claim 20, wherein the PcTs is selected from the group of metal-free PcTS, PcTS-$Fe^{3+}$, PcTS-$Mn^{3+}$, PcTS-$Co^{3+}$, PcTS-$Cu^{2+}$, PcTS-$Ni^2+$ and PcTS-VO.

22. The method of claim 10, wherein the tetrapyrrole is a deuteroporphyrin.

23. The method of claim 22 wherein the deuteroporphyrin is substituted with a sulfate or a hydroxyalkyl group.

24. The method of claim 23, wherein the hydroxyalkyl group is a polyol.

25. The method of claim 22, wherein the deuteroporphyrin is complexed with a metal.

26. The method of claim 23, wherein the metal is an iron ion.

27. The method of claim 26, wherein the iron ion is $Fe^{3+}$.

28. The method of claim 10, wherein the tetrapyrrole is a meso-substituted porphine.

29. The method of claim 28, wherein the porphine is meso-substituted with a substituted or unsubstituted phenyl or pyridyl group.

30. The method of claim 29, wherein the phenyl or pyridyl is substituted with an oxygen substituted sulfur, an alkyl substituted nitrogen, or alkyl.

31. The method of claim 20, wherein the a phenyl of the PcTs is substituted with a sulfonyl or trimethylamine, and a pyridyl of the PcTs is substituted on the nitrogen with a lower alky.

32. The method of claim 28, wherein the porphine is a metalloporphine.

33. The method of claim 32, wherein the metalloporphine is complexed with a metal selected from the group of iron, manganese, copper, nickel and zinc.

34. The method of claim 1 wherein the tetrapyrrole is complexed with a metal.

35. The method of claim 34 wherein the tetrapyrrole is complexed with a metal cation.

36. The method of claim 1 wherein the amount of the tetrapyrrole administered is between 1 nanogram and 1 gram per kg body weight of the animal.

37. The method of claim 36 wherein the amount of the tetrapyrrole administered is between 1 microgram and 100 micrograms per kg body weight of the animal.

38. The method of claim 35 wherein the cation is selected from the group consisting of: $Fe^{3+}$, $Mn^{3+}$, $Co^{3+}$, $Cu^{2+}$, $Ni^+$, $Zn^{2+}$, $Co^2+$ and $Al^{3+}$.

39. The method of claim 34 wherein the tetrapyrrole is complexed with a VO compound.

40. The method of claim 1 wherein the tetrapyrrole is administered by a route selected from the group consisting of direct administration into the CNS, intracranial ventricular, intrathecal, aural, transdermal, intravenous, intramuscular, subcutaneous, oral, olfactory, ocular and rectal.

41. The method of claim 1, wherein the tetrapyrrole is administered prophylactically to inhibit infection with a spongiform encephalopathy.

42. A method of inhibiting the conversion of PrP-sen to PrP-res comprising contacting the PrP-sen with a tetrapyrrole.

43. The method of claim 42 wherein the tetrapyrrole is selected from the group consisting of a porphyrin, a phthalocyanine, a deuteroporphyrin, a meso-substituted porphyrin and a phthalocyanine sulphonate.

44. The method of claim 42 wherein the PrP-sen is present in an animal cell and wherein the tetrapyrrole is administered to the cell.

45. The method of claim 1 wherein the tetrapyrrole is selected from the group consisting of:

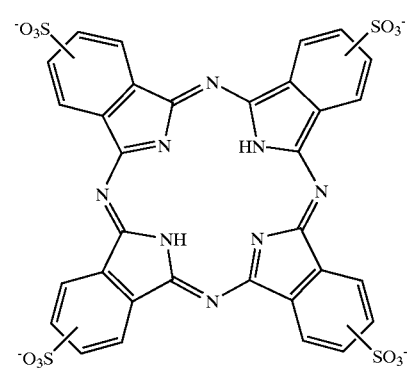

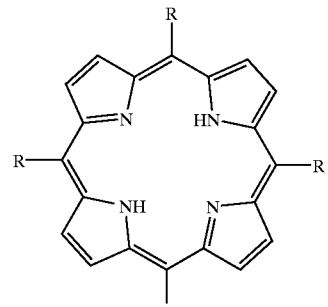

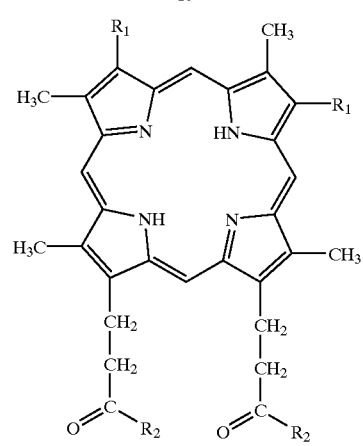

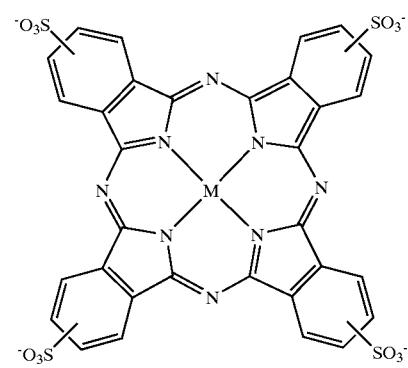

-continued

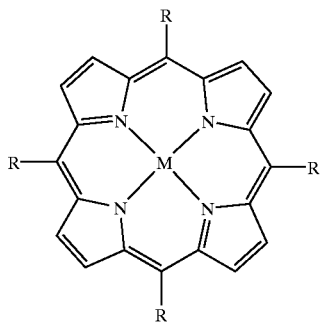

and wherein M is selected from the group consisting of: $Fe^{3+}$, $Mn^{3+}$, $Co^{3+}$, $Co^{2+}$, $AL^{3+}$, $Cu2+$, $Ni^{2+}$, $Zn^{2+}$ and VO; and wherein R is selected from the group consisting of:

where y is $SO_3^-$, $CO_2^-$, hydroxy, alkoxy, or 2°, 3°, or 4° amine or

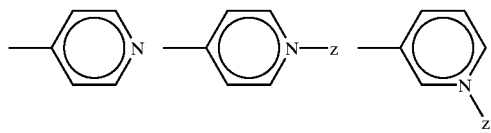

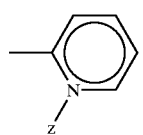

where z is $C_1$ to $C_5$ alkyl.

and wherein $R_1$ is selected from the group consisting of:

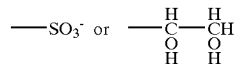

and wherein $R_2$ is selected from the group consisting of:

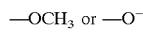

46. The method of claim 45 where the tetrapyrrole is metal-free.

47. The method of claim 45 where the tetrapyrrole is:

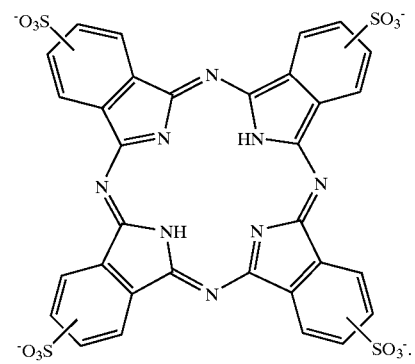

48. The method of claim 45 where the tetrapyrrole is:

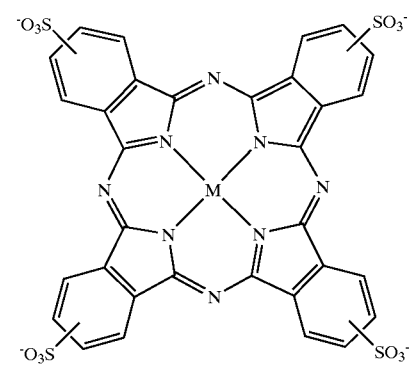

and where M is selected from the group consisting of $Fe^{3+}$, $Mn^{3+}$, $Co^{3+}$, $Co^{2+}$, $AL^{3+}$, $Cu^{2+}$, $Ni^{2+}$, $Zn^{2+}$, and VO.

49. The method of claim 45 where the tetrapyrrole is:

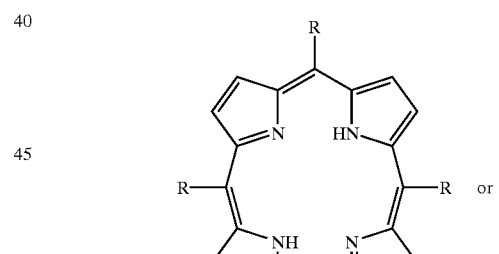

or

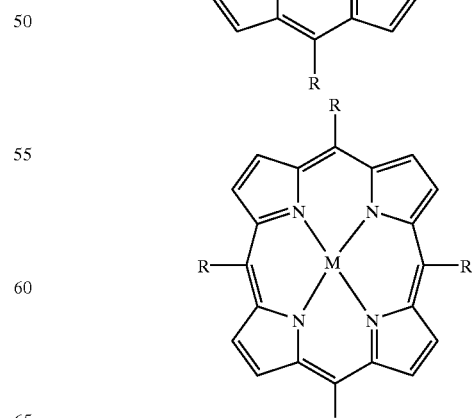

and wherein M is $Fe^{3+}$, $Mn^{3+}$, $Cu^{2+}$, $Ni^{2+}$ or $Zn^{2+}$, and R is

where y is $SO_3^-$, $CO_2^-$, hydroxy, alkoxy, or $2^{602}$, $3^{602}$, or $4^{602}$ amine or

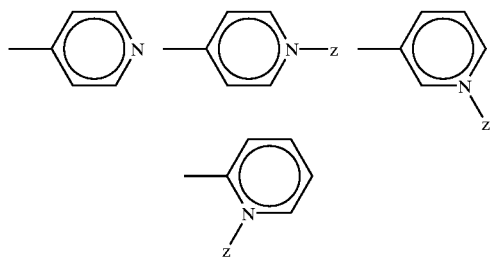

where z is $C_1$ to $C_5$ alkyl.

50. The method of claim 49 wherein z is methyl.

51. The method of claim 45 wherein the tetrapyrrole is

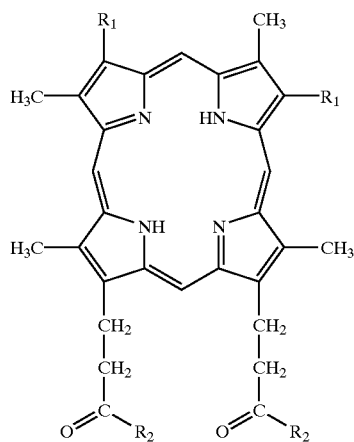

wherein $R_1$ is $SO_3$ or a glycol and $R_2$ is O or O—Z where Z is alkyl.

52. The method of claim 51 where Z is methyl.

53. The method of claim 52 where the tetrapyrrole is complexed with a metal.

54. The method of claim 53 where the metal is $Fe^{3+}$.

55. A method for inhibiting progression of an amyloidogenic disease in an animal comprising administering a therapeutically effective amount of a tetrapyrrole to the animal, the tetrapyrrole comprising a phthalocyanine, a tetrapyrrole comprising VO or a meso-substituted porphine.

56. The method of claim 55, wherein the tetrapyrrole comprises a phthalocyanine.

57. The method of claim 56, wherein the phthalocyanine comprises a phthalocyanine sulfonate.

58. The method of claim 57, wherein the phthalocyanine comprises a phthalocyanine monosulfonate, disulfonate, trisulfonate or tetrasulfonate.

59. The method of claim 56, wherein the phthalocyanine comprises a metallophthalocyanine.

60. The method of claim 59, wherein the metallophthalocyanine comprises a transition metal.

61. The method of claim 59, wherein the metallophthalocyanine comprises a metal selected from the group of iron, manganese, cobalt, nickel, zinc, vanadium, and aluminum.

62. The method of claim 59, wherein the metallophthalocyanine comprises an ion selected from the group of $Fe^{3+}$, $Mn^{3+}$, $Co^{3+}$, $Cu^{2+}$, $Ni^{2+}$, $Zn^{2+}$, $Co^{2+}$, VO and $Al^{3+}$.

63. The method of claim 62, wherein the ion is selected from the group consisting of $Fe^{3+}$, $Mn^{3+}$, $Co^{3+}$, $Cu^{2+}$, $Ni^{2+}$, VO, and $Zn^{2+}$.

64. The method of claim 57 wherein the phthalocyanine is a tetrasulfonylphthalocyanine.

65. The method of claim 64 wherein the tetrasulfonylphthalocyanine is selected from the group of metal-free PcTS, PcTS-$Fe^{3+}$, PcTS-$Mn^{3+}$, PcTS-$Co^{3+}$, PcTS-$Cu^{2+}$, PcTS-$Ni^{2+}$ and PcTS-VO.

66. The method of claim 55, wherein the tetrapyrrole is a meso-substituted porphine.

67. The method of claim 66, wherein the porphine is meso-substituted with a substituted or unsubstituted phenyl or pyridyl group.

68. (New) The method of claim 67, wherein the phenyl or pyridyl is substituted with an oxygen substituted sulfur, an alkyl substituted nitrogen, or alkyl.

69. The method of claim 68, wherein the phenyl is substituted with a sulfonyl or trimethylamine, and the pyridyl is substituted on the nitrogen with a lower alkyl.

70. The method of claim 55, wherein the tetrapyrrole comprises VO.

* * * * *

UNITED STATES PATENT AND TRADEMARK OFFICE
CERTIFICATE OF CORRECTION

PATENT NO. : 6,632,808 B1
DATED : October 14, 2003
INVENTOR(S) : Caughey et al.

It is certified that error appears in the above-identified patent and that said Letters Patent is hereby corrected as shown below:

Title page,
Item [56], References Cited, OTHER PUBLICATIONS, insert the following omitted reference -- Vincent et al., "A protein kinase associated with paired helical filaments in Alzheimer disease," *Proc. Natl. Acad. Sci. USA*, 89:2878-2882 (1992). --.
Item [57], ABSTRACT,
Line 11, "PrP-sen to PrP-sen" should read -- PrP-sen to PrP-res --.

Column 1,
Line 53, "(BES), latrogenic" should read -- (BES). Iatrogenic --.

Column 2,
Line 30, "471474" should read -- 471-474 --.
Line 37, "49314936" should read -- 4931-4936 --.

Column 3,
Line 12, "1997" should read -- 1997, --.
Line 27, "399-344" should read -- 399-444 --.
Line 62, "deratives" should read -- derivatives --.

Column 4,
Line 19, "deposits" should read -- deposits --.
Line 19, "Alzheimer□s disease" should read -- Alzheimer's disease --.
Lines 50-51, "postitions" should read -- positions --.
Line 54, "group,a" should read -- group, a --.

Column 5,
Line 57, "PcTS-Al$^3$+" should read -- PcTS-Al$^{3+}$ --.
Line 58, "GdncHcl" should read -- GdnHCl --.

Column 6,
Line 5, "pthalocyanines" should read -- phthalocyanines --.

Column 7,
Line 65, "immomglobulin" should read -- immunoglobulin --.

Column 8,
Lines 37, 54 and 64, "aryloxy, aryloxy" should read -- aryloxy --.

UNITED STATES PATENT AND TRADEMARK OFFICE
CERTIFICATE OF CORRECTION

PATENT NO.    : 6,632,808 B1
DATED         : October 14, 2003
INVENTOR(S)   : Caughey et al.

It is certified that error appears in the above-identified patent and that said Letters Patent is hereby corrected as shown below:

Column 9,
Line 7, "subustituent" should read -- substituent --.
Line 63, "piperazin-1-_yl," should read -- piperazin-1-yl --.

Column 10,
Line 1, "Example" should read -- Examples --.
Lines 66-67, "t postitions" should read -- β positions --.

Column 11,
Line 26, "position" should read -- position --.
Line 65, "cartonyl" should read -- carbonyl --.
Line 65, "carhoxylic" should read -- carboxylic --.
Line 66, "a.ides" should read -- amides --.

Column 12,
Line 41, "phospato" should read -- phosphato --.

Column 14,
Line 8, "(PcTs)" should read -- (PcTS) --.
Line 9, "respectively" should read -- respectively. --.

Column 17,
Line 42, "Mn3+" should read -- $Mn^{3+}$ --.

Column 18,
Line 43, "IC50" should read -- $IC_{50}$ --.

Column 22,
Line 1, "Me4" should read -- Me-4 --.

Column 23,
Line 19, "(mean☐SD)" should read -- (mean ± SD) --.
Line 22, "4NMe₃⁺" should read -- $4\text{-NMe}_3^+$ --.
Line 47, "ethers, such" should read -- ethers, such --.
Line 54, "$C_{15}$" should read -- $C_{1-5}$ --.
Lines 56 and 57, "C1-5" should read -- $C_{1-5}$ --.
Line 59, "phorphines" should read -- porphines --.

UNITED STATES PATENT AND TRADEMARK OFFICE
CERTIFICATE OF CORRECTION

PATENT NO. : 6,632,808 B1
DATED : October 14, 2003
INVENTOR(S) : Caughey et al.

It is certified that error appears in the above-identified patent and that said Letters Patent is hereby corrected as shown below:

Column 25,
Line 28, "type 11" should read -- type II --.

Column 26,
Line 34, "disease" should read -- disease. --.
Line 66, "treatmentis" should read -- treatment is --.

Column 28,
Line 44, "miethod" should read -- method --.
Line 44, "te" should read -- the --.
Line 45, "deuteroporphynn" should read -- deuteroporphyrin --.
Line 46, "potphine" should read -- porphine --.
Line 46, "phthalocyanina" should read -- phthalocyanine --.
Line 47, "wherin" should read -- wherein --.
Line 49, "progession" should read -- progression --.
Line 63, "claim 16" should read -- claim 15 --.

Column 29,
Line 6, "$Zn^2+$" should read -- $Zn^{2+}$ --.
Lines 8 and 9, "(PcTs)" should read -- (PcTS) --.
Line 11, "$Ni^2+$" should read -- $Ni^{2+}$ --.
Line 19, "claim 23" should read -- claim 25 --.
Line 30, "the a" should read -- a --.
Line 33, "alky" should read -- alkyl --.

Column 30,
Line 2, "sulphonate" should read -- sulfonate --.

Column 31,
Line 20, "$AL^3$" should read -- $Al^{3+}$ --.
Line 20, "Cu2+" should read -- $Cu^{2+}$ --.

Column 32,
Line 37, "$AL^{3+}$" should read -- $Al^{3+}$ --.

UNITED STATES PATENT AND TRADEMARK OFFICE
CERTIFICATE OF CORRECTION

PATENT NO. : 6,632,808 B1
DATED : October 14, 2003
INVENTOR(S) : Caughey et al.

It is certified that error appears in the above-identified patent and that said Letters Patent is hereby corrected as shown below:

Column 33,
Lines 7-8, "$2^{602}$, $3^{602}$, or $4^{602}$" should read -- $2^o$, $3^o$, or $4^o$ --.
Line 43, "$SO_3$" should read -- $SO_3$ --.
Line 46, "claim 52" should read -- claim 43 --.

Column 34,
Line 38, delete "(New)".

Signed and Sealed this

Twenty-first Day of September, 2004

JON W. DUDAS
*Director of the United States Patent and Trademark Office*